United States Patent
Fujita et al.

(10) Patent No.: US 11,424,417 B2
(45) Date of Patent: Aug. 23, 2022

(54) ORGANIC ELECTROLUMINESCENCE DEVICE AND COMPOUND FOR ORGANIC ELECTROLUMINESCENCE DEVICE

(71) Applicant: SAMSUNG DISPLAY CO., LTD., Yongin-si (KR)

(72) Inventors: Yoshimasa Fujita, Yokohama (JP); Keigo Hoshi, Yokohama (JP); Yuuki Miyazaki, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 412 days.

(21) Appl. No.: 16/567,389

(22) Filed: Sep. 11, 2019

(65) Prior Publication Data

US 2020/0161562 A1    May 21, 2020

(30) Foreign Application Priority Data

Nov. 16, 2018 (KR) .................. 10-2018-0141922

(51) Int. Cl.
| | | |
|---|---|---|
| *H01L 51/00* | (2006.01) | |
| *C07D 209/86* | (2006.01) | |
| *C09K 11/06* | (2006.01) | |
| *H01L 51/50* | (2006.01) | |
| *H01L 51/56* | (2006.01) | |

(52) U.S. Cl.
CPC ........ *H01L 51/0072* (2013.01); *C07D 209/86* (2013.01); *C09K 11/06* (2013.01); *C09K 2211/1018* (2013.01); *H01L 51/001* (2013.01); *H01L 51/5012* (2013.01); *H01L 51/56* (2013.01); *H01L 2251/558* (2013.01)

(58) Field of Classification Search
USPC ........................................ 428/690
See application file for complete search history.

(56) References Cited

U.S. PATENT DOCUMENTS

| | | | |
|---|---|---|---|
| 6,562,982 B1 | 5/2003 | Hu et al. | |
| 6,670,054 B1 | 12/2003 | Hu et al. | |
| 8,609,257 B2 | 12/2013 | Ise et al. | |
| 9,029,487 B2 | 5/2015 | Klosin et al. | |
| 9,246,111 B1 | 1/2016 | Kim et al. | |
| 9,273,000 B2 | 3/2016 | Hayashi et al. | |
| 9,401,484 B2 | 7/2016 | Kim et al. | |
| 10,193,079 B2 | 1/2019 | Stoessel et al. | |
| 11,121,184 B2 * | 9/2021 | Song .................. | H01L 51/504 |
| 11,136,294 B2 | 10/2021 | Bergmann et al. | |
| 2002/0125818 A1 | 9/2002 | Sato et al. | |
| 2003/0218418 A9 | 11/2003 | Sato et al. | |
| 2012/0126691 A1 | 5/2012 | Ise et al. | |
| 2012/0126692 A1 | 5/2012 | Ise et al. | |
| 2013/0292654 A1 | 11/2013 | Matsunaga et al. | |
| 2014/0264292 A1 | 9/2014 | Xia et al. | |
| 2015/0105564 A1 | 4/2015 | Adachi et al. | |
| 2016/0087222 A1 | 3/2016 | Huang et al. | |
| 2016/0111652 A1 | 4/2016 | Huang et al. | |
| 2016/0126478 A1 | 5/2016 | Zheng et al. | |
| 2016/0301015 A1 | 10/2016 | Zheng et al. | |
| 2016/0315269 A1 | 10/2016 | Xia et al. | |
| 2017/0098780 A1 | 4/2017 | Kim et al. | |
| 2017/0125699 A1 | 5/2017 | Ahn et al. | |
| 2017/0186973 A1 | 6/2017 | Ren et al. | |
| 2017/0352816 A1 | 12/2017 | Jeon et al. | |
| 2018/0026202 A1 | 1/2018 | Danz et al. | |
| 2018/0108857 A1 | 4/2018 | Adachi et al. | |
| 2018/0170914 A1 | 6/2018 | Miyata et al. | |
| 2018/0198075 A1 | 7/2018 | Danz et al. | |
| 2018/0212158 A1 | 7/2018 | Aspuru-Guzik et al. | |
| 2018/0248127 A1 * | 8/2018 | Lee .................. | C09K 11/06 |
| 2019/0013481 A1 * | 1/2019 | Nasu .................. | C07D 209/86 |
| 2019/0016704 A1 | 1/2019 | Nasu et al. | |
| 2019/0103564 A1 * | 4/2019 | Ogawa ................ | H01L 51/0052 |
| 2019/0198778 A1 | 6/2019 | Bergmann et al. | |
| 2019/0198779 A1 | 6/2019 | Bergmann et al. | |
| 2019/0393428 A1 | 12/2019 | Seifermann | |
| 2020/0119287 A1 * | 4/2020 | Aguilera-Iparraguirre .................. | C09K 11/06 |
| 2021/0119146 A1 * | 4/2021 | Hong .................. | H01L 51/0056 |
| 2021/0155849 A1 * | 5/2021 | Stubbs ............... | C09K 11/0883 |

FOREIGN PATENT DOCUMENTS

| | | |
|---|---|---|
| CN | 103180347 A | 6/2013 |
| CN | 104119274 A | 10/2014 |
| CN | 104119861 A | 10/2014 |
| CN | 102792777 B | 12/2015 |
| CN | 105294905 A | 2/2016 |
| CN | 106164046 A | 11/2016 |

(Continued)

OTHER PUBLICATIONS

CAS reg. No. 2418657-54-0, Jun. 3, 2020. (Year: 2020).*

(Continued)

*Primary Examiner* — Douglas J McGinty
(74) *Attorney, Agent, or Firm* — Lewis Roca Rothgerber Christie LLP

(57) ABSTRACT

An organic electroluminescence device includes a first electrode, a second electrode on the first electrode, and an emission layer between the first electrode and the second electrode. The emission layer may include a compound including a first phenyl group that is substituted with at least one cyano group and a second phenyl group that is substituted with five substituted or unsubstituted carbazole groups, the second phenyl group being directly bonded to the first phenyl group.

20 Claims, 2 Drawing Sheets

(56) References Cited

FOREIGN PATENT DOCUMENTS

| | | |
|---|---|---|
| CN | 106316924 A | 1/2017 |
| CN | 106488965 A | 3/2017 |
| CN | 107074765 A | 8/2017 |
| CN | 107302844 A | 10/2017 |
| CN | 107925004 A | 4/2018 |
| CN | 107954922 A | 4/2018 |
| CN | 107987009 A | 5/2018 |
| DE | 102016108334 B3 | 12/2016 |
| DE | 102016108335 B3 | 12/2016 |
| DE | 102016108332 B3 | 2/2017 |
| DE | 102016108327 B3 | 3/2017 |
| DE | 102016110004 B3 | 4/2017 |
| DE | 102016112082 A1 | 1/2018 |
| DE | 102017103542 B3 | 3/2018 |
| EP | 2609123 | 7/2013 |
| EP | 2711359 A1 | 3/2014 |
| EP | 2711949 A1 | 3/2014 |
| EP | 2712859 A2 | 4/2014 |
| EP | 2712860 A1 | 4/2014 |
| EP | 3113239 A1 | 1/2017 |
| EP | 3131879 | 2/2017 |
| EP | 3138137 | 3/2017 |
| EP | 2549837 B1 | 2/2018 |
| EP | 3317904 | 5/2018 |
| ES | 2659733 T3 | 3/2018 |
| JP | 5-32625 A | 2/1993 |
| JP | 8-60144 A | 3/1996 |
| JP | 8-88083 A | 4/1996 |
| JP | 2001-313179 A | 11/2001 |
| JP | 2003-31371 A | 1/2003 |
| JP | 2003-77674 A | 3/2003 |
| JP | 4474493 B1 | 6/2010 |
| JP | 4523992 B1 | 8/2010 |
| JP | 2011-044365 A | 3/2011 |
| JP | 4729642 B1 | 7/2011 |
| JP | 2011-176250 A | 9/2011 |
| JP | 2011-176258 A | 9/2011 |
| JP | 2011-192524 A | 9/2011 |
| JP | 2011-216455 A | 10/2011 |
| JP | 2014-506262 A | 3/2014 |
| JP | 2014-94935 A | 5/2014 |
| JP | 2014-135466 A | 7/2014 |
| JP | 2015-043435 A | 3/2015 |
| JP | 2015-107982 A | 6/2015 |
| JP | 2015-107983 A | 6/2015 |
| JP | 2015-110591 A | 6/2015 |
| JP | 5914514 B2 | 5/2016 |
| JP | 2016-516085 A | 6/2016 |
| JP | 2016-520253 A | 7/2016 |
| JP | 2016-523990 A | 8/2016 |
| JP | 2016-526025 A | 9/2016 |
| JP | 5989078 B2 | 9/2016 |
| JP | 2016-539182 A | 12/2016 |
| JP | 6133494 B2 | 5/2017 |
| JP | 2017-103440 A | 6/2017 |
| JP | 2017-514302 A | 6/2017 |
| JP | 2017-119663 A | 7/2017 |
| JP | 2017-119664 A | 7/2017 |
| JP | 2018-505126 A | 2/2018 |
| KR | 10-2011-088427 A | 8/2011 |
| KR | 10-2011-0088457 A | 8/2011 |
| KR | 10-2012-0018231 A | 2/2012 |
| KR | 10-2012-0025008 A | 3/2012 |
| KR | 10-2012-0137321 A | 12/2012 |
| KR | 10-2013-0016267 A | 2/2013 |
| KR | 10-2013-0100140 A | 9/2013 |
| KR | 10-2014-0113483 A | 9/2014 |
| KR | 10-1502316 B1 | 3/2015 |
| KR | 10-2015-0132872 A | 11/2015 |
| KR | 10-2016-0007965 A | 1/2016 |
| KR | 10-2016-0007966 A | 1/2016 |
| KR | 10-2016-0028406 A | 3/2016 |
| KR | 10-2016-0030094 A | 3/2016 |
| KR | 10-2016-0030877 A | 3/2016 |
| KR | 10-2017-0015414 A | 2/2017 |
| KR | 10-2017-0040697 A | 4/2017 |
| KR | 10-1738607 B1 | 5/2017 |
| KR | 10-2017-0087845 A | 7/2017 |
| KR | 10-2017-0088822 A | 8/2017 |
| KR | 10-2017-0092138 A | 8/2017 |
| KR | 10-1772548 B1 | 8/2017 |
| KR | 10-1781114 B1 | 9/2017 |
| KR | 10-2017-0136256 A | 12/2017 |
| KR | 10-2018-0008154 A | 1/2018 |
| KR | 10-2018-0023969 A | 3/2018 |
| KR | 10-1831270 B1 | 4/2018 |
| KR | 10-2018-0066258 A | 6/2018 |
| KR | 10-2018-0098809 A | 9/2018 |
| TW | I480359 B | 4/2015 |
| TW | I498411 B | 9/2015 |
| TW | I541239 B | 7/2016 |
| TW | I541323 B | 7/2016 |
| WO | WO 2011/013843 A1 | 2/2011 |
| WO | WO 2011/013859 A1 | 2/2011 |
| WO | WO 2011/021433 A1 | 2/2011 |
| WO | WO 2011/114833 A1 | 9/2011 |
| WO | WO 2011/114886 A1 | 9/2011 |
| WO | WO 2012/005172 A1 | 1/2012 |
| WO | WO 2012/027448 A1 | 3/2012 |
| WO | WO 2012/078005 A2 | 6/2012 |
| WO | WO 2014/173323 A1 | 10/2014 |
| WO | WO 2014/173324 A1 | 10/2014 |
| WO | 2014/183080 A1 | 11/2014 |
| WO | WO 2015/066354 A1 | 5/2015 |
| WO | WO 2015/160224 A1 | 10/2015 |
| WO | WO 2016/138077 A1 | 9/2016 |
| WO | WO 2016/152605 A1 | 9/2016 |
| WO | 2016/181846 A1 | 11/2016 |
| WO | WO 2017/005698 A1 | 1/2017 |
| WO | WO 2017/005699 A1 | 1/2017 |
| WO | WO 2017/011531 A2 | 1/2017 |
| WO | 2017/169497 A1 | 10/2017 |
| WO | WO 2017/190885 A1 | 11/2017 |
| WO | WO 2018/001820 A1 | 1/2018 |
| WO | WO 2018/001821 A1 | 1/2018 |
| WO | WO 2018/001822 A1 | 1/2018 |
| WO | WO 2018/037069 A1 | 3/2018 |

OTHER PUBLICATIONS

H. Noda et al., "Excited state engineering for efficient reverse intersystem crossing", Science Advances, 2018, 4, pp. 1-7.
Yuan, Wenbo et al., "The electron inductive effect of CF3 on penta-carbazole containing blue emitters: Trade-off between color purity and luminescent efficiency in TADF OLEDs," Dyes and Pigments, vol. 159, 2018, 7 pages.
EPO Extended Search Report dated Dec. 18, 2019, for corresponding European Patent Application No. 19206317.0 (8 pages).

* cited by examiner

ORGANIC ELECTROLUMINESCENCE DEVICE AND COMPOUND FOR ORGANIC ELECTROLUMINESCENCE DEVICE

CROSS-REFERENCE TO RELATED APPLICATION

Korean Patent Application No. 10-2018-0141922, filed on Nov. 16, 2018, in the Korean Intellectual Property Office, and entitled: "Organic Electroluminescence Device and Compound for Organic Electroluminescence Device," is incorporated by reference herein in its entirety.

BACKGROUND

1. Field

Embodiments relate to an organic electroluminescence device and a compound used therein.

2. Description of the Related Art

Recently, the development of an organic electroluminescence display device as an image display device is being actively conducted. Different from a liquid crystal display device, the organic electroluminescence display device is so-called a self-luminescent display device in which holes and electrons injected from a first electrode and a second electrode recombine in an emission layer, and a light-emitting material including an organic compound in the emission layer emits light to attain display.

SUMMARY

Embodiments are directed to an organic electroluminescence device, including a first electrode, a second electrode on the first electrode, and an emission layer between the first electrode and the second electrode. The emission layer may include a compound including a first phenyl group that is substituted with at least one cyano group and a second phenyl group that is substituted with five substituted or unsubstituted carbazole groups, the second phenyl group being directly bonded to the first phenyl group.

The at least one cyano group may substituted on the first phenyl group at a para position or a meta position with respect to the second phenyl group.

The five substituted or unsubstituted carbazole groups may be selected from an unsubstituted carbazole group, a carbazole group that is substituted with an aryl group of 6 to 18 ring carbon atoms, or a carbazole group that is substituted with a heteroaryl group of 5 to 18 ring carbon atoms.

The second phenyl group may be substituted with at least one of a carbazole group that is substituted with a phenyl group, or a carbazole group that is substituted with a pyridine group.

The compound may be represented by the following Formula 1:

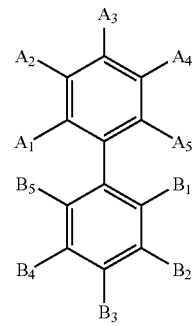

[Formula 1]

wherein, in Formula 1, at least one among $A_1$ to $A_5$ may be a cyano group, and the rest may each independently be a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, at least one among $B_1$ to $B_5$ may be represented by the following Formula 2-1 and the rest may be represented by the following Formula 2-2:

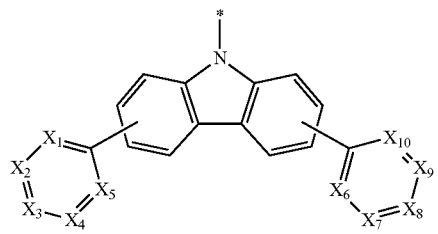

[Formula 2-1]

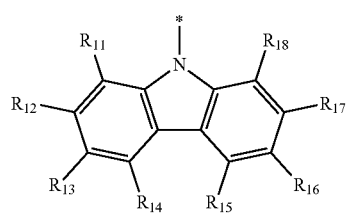

[Formula 2-2]

wherein, in Formula 2-1, $X_1$ to $X_{10}$ may each independently be N or $CR_1$, and $R_1$ may be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, wherein, in Formula 2-2, $R_{11}$ to $R_{18}$ may each independently be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms.

Formula 1 may be represented by any one among the following Formula 1-1 to Formula 1-3:
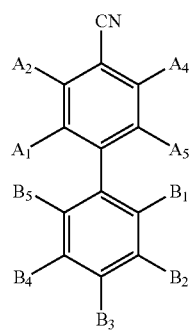
[Formula 1-1]
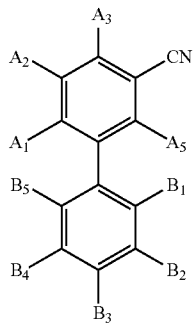
[Formula 1-2]
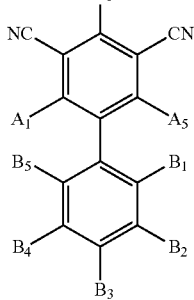
[Formula 1-3]
wherein, in Formula 1-1 to Formula 1-3, $A_1$ to $A_5$, and $B_1$ to $B_5$ are the same as defined in Formula 1.
Formula 1 may be represented by the following Formula 1-4 or Formula 1-5:
[Compound 1-4]

[Formula 1-5]

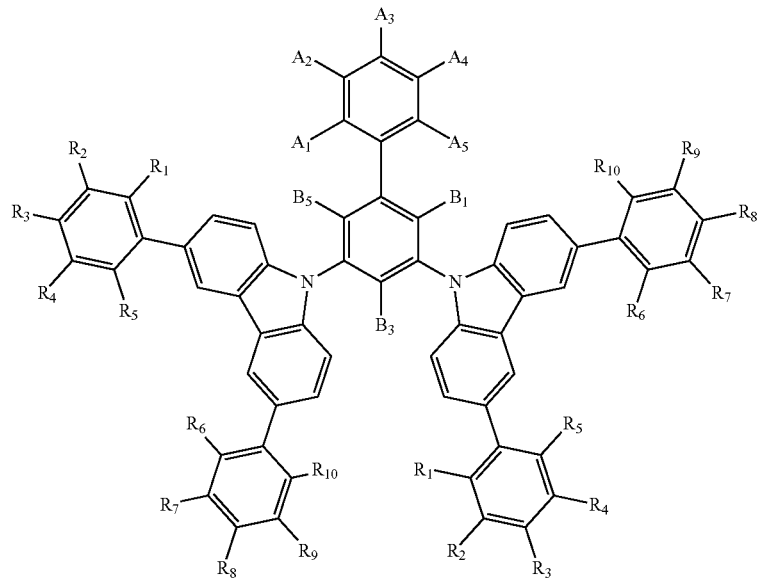

wherein, in Formula 1-4, $B_2$ and $B_4$ may be represented by Formula 2-2, in Formula 1-5, $B_1$, $B_3$, and $B_5$ may be represented by Formula 2-2, and in Formula 1-4 and Formula 1-5, $A_1$ to $A_5$ may be the same as defined in Formula 1.

Formula 2-1 may be represented by the following Formula 2-1A or Formula 2-1B, and Formula 2-2 may be represented by the following Formula 2-2A:

[Formula 2-1A]

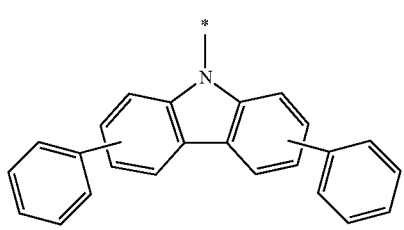

[Formula 2-1B]

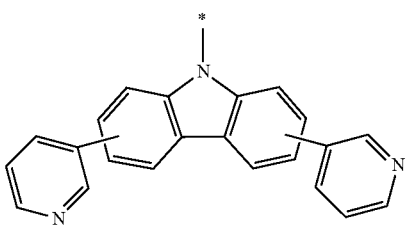

[Formula 2-2A]

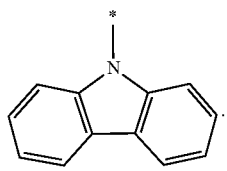

The emission layer may emit light by delayed fluorescence.

The emission layer may be a delayed fluorescence emission layer including a host and a dopant, and the dopant may include the compound.

The emission layer may emit blue light having a central wavelength $\lambda_{max}$ of 430 nm to 490 nm.

The emission layer may include at least one among compounds in the following Compound Group 1:
[Compound Group 1]
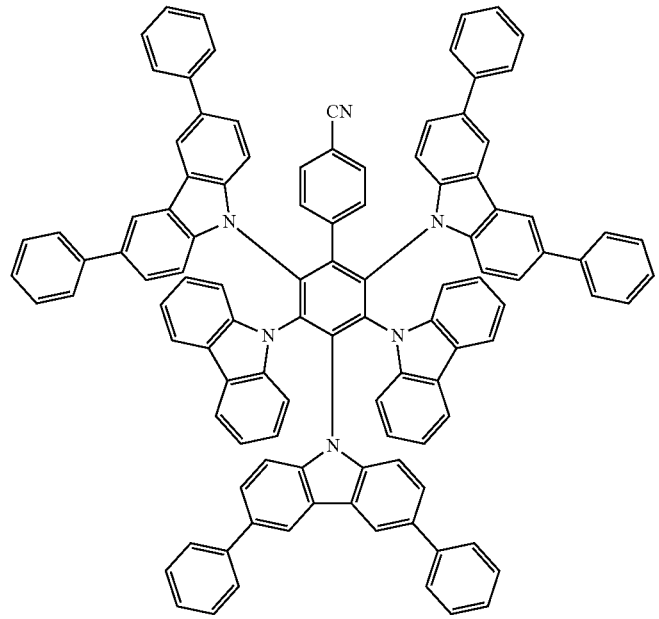
1
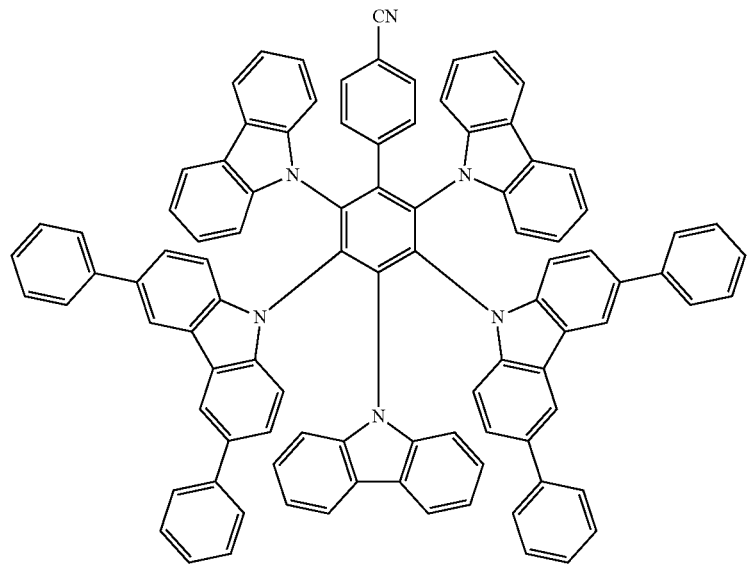
2

-continued
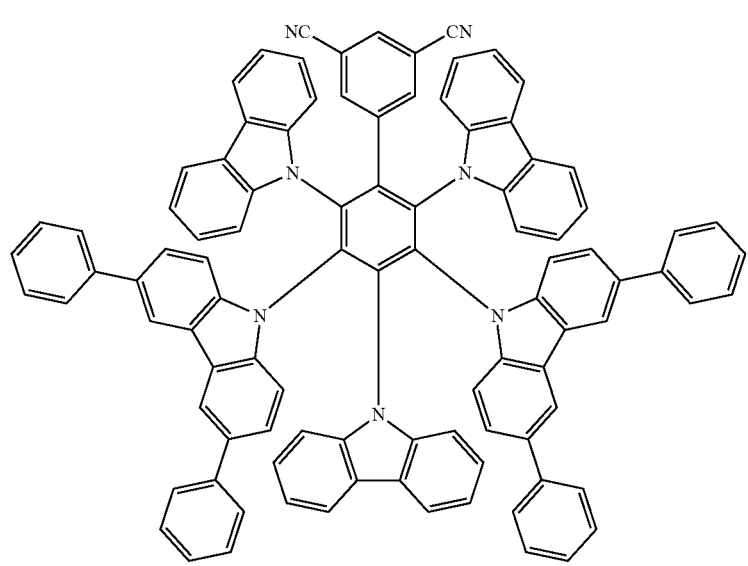
3
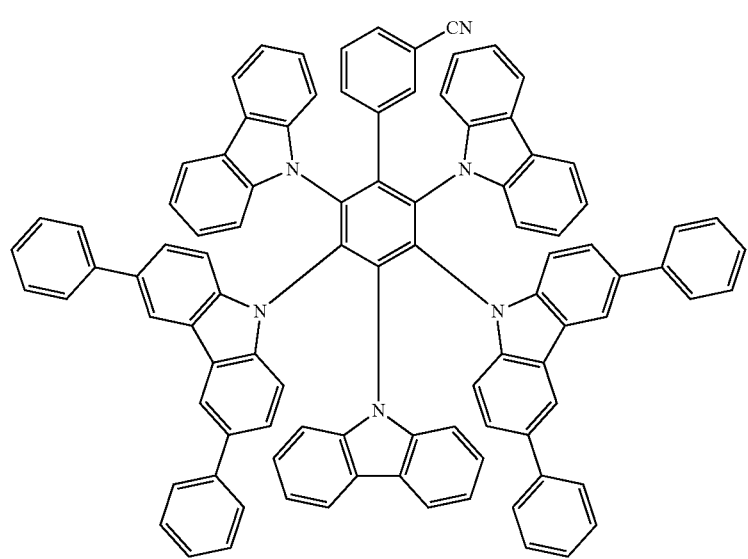
4

-continued
5
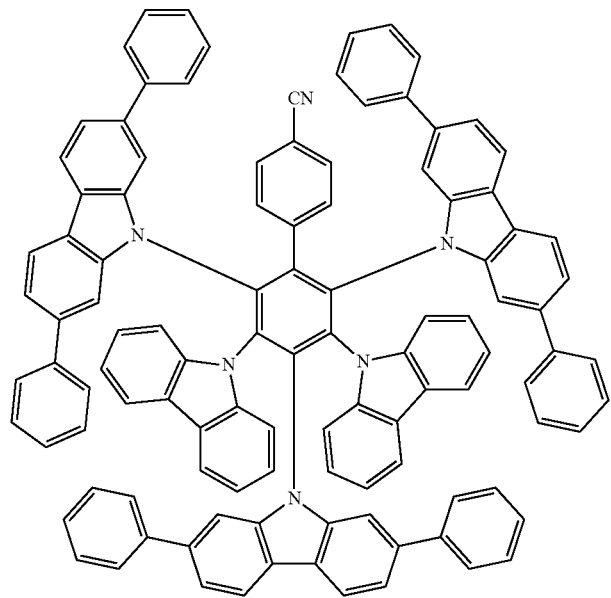
6
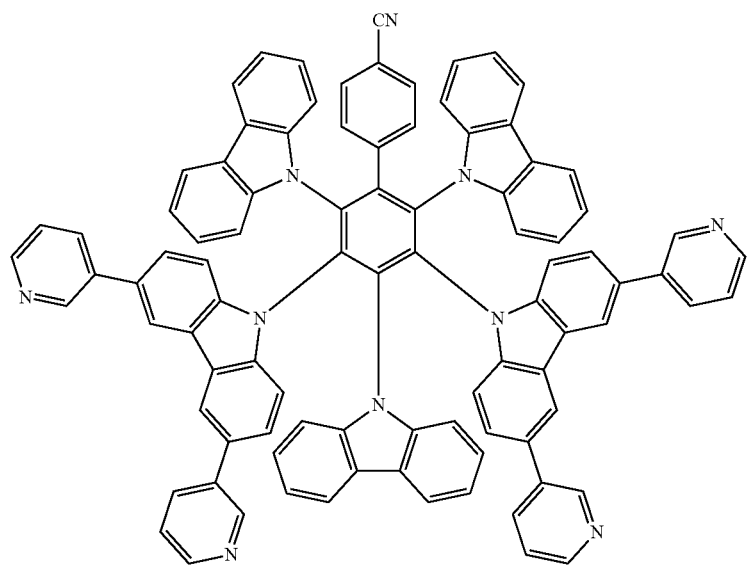

-continued
7
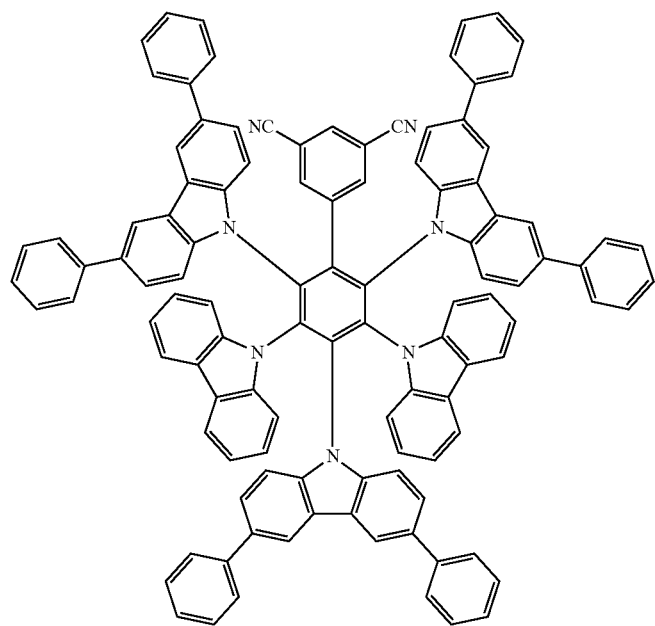
8
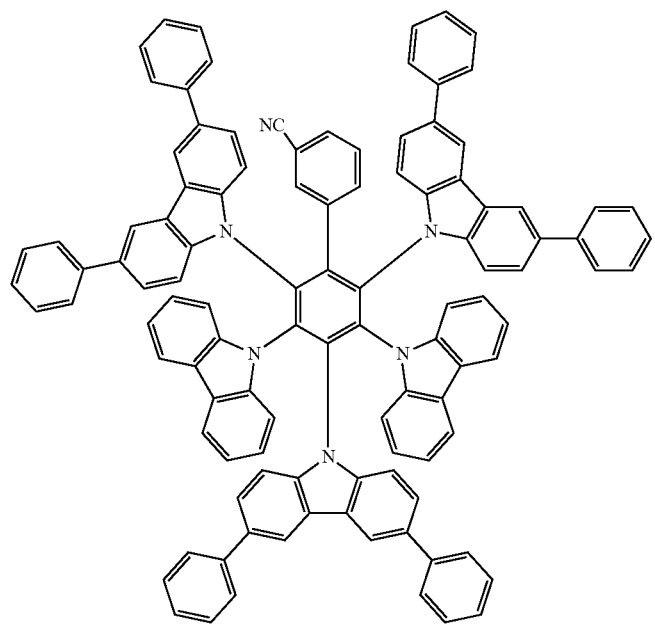

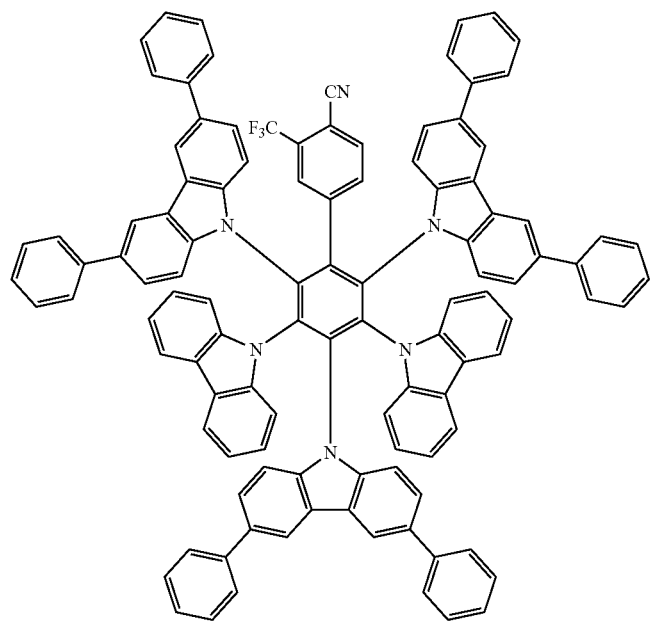
9
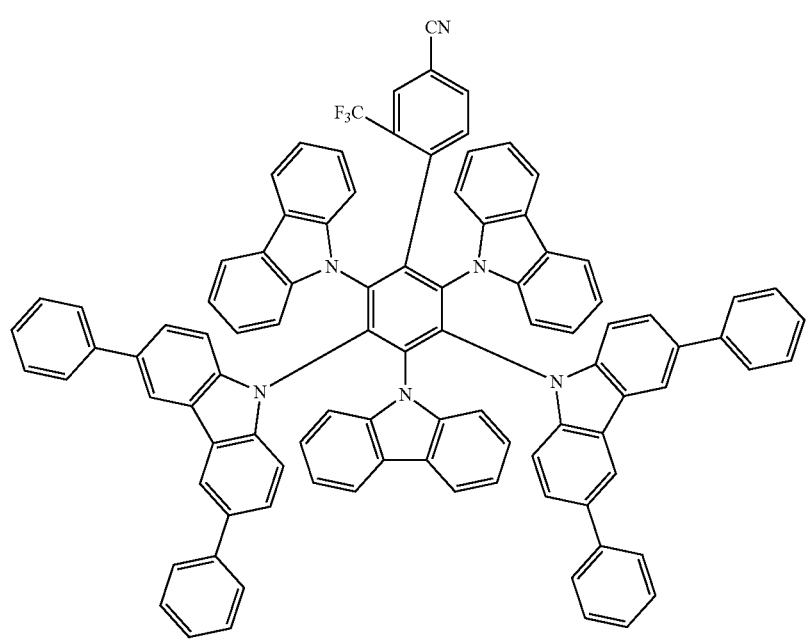
10

-continued

11

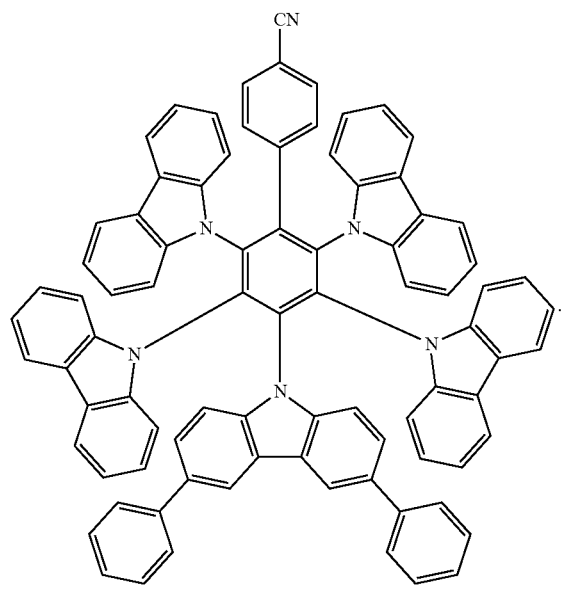

Embodiments are also directed to an organic electroluminescence device, including a first electrode, a second electrode on the first electrode, and an emission layer between the first electrode and the second electrode, the emission layer including a compound represented by the following Formula 1:

[Formula 1]

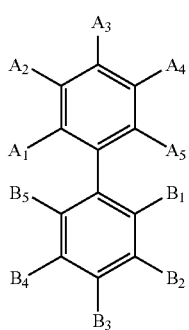

wherein, in Formula 1, at least one among $A_1$ to $A_5$ may be a cyano group, and the rest may each independently be a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, at least one among $B_1$ to $B_5$ may be represented by the following Formula 2-1 and the rest may independently be represented by the following Formula 2-2:

[Formula 2-1]

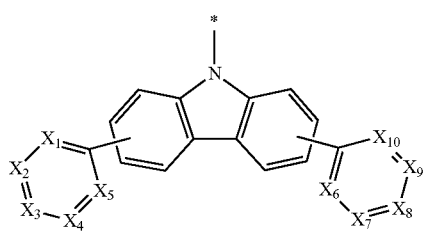

[Formula 2-2]

wherein, in Formula 2-1, $X_1$ to $X_{10}$ may each independently be N or $CR_1$, and $R_1$ may be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, wherein, in Formula 2-2, $R_{11}$ to $R_{18}$ may each independently be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms.

The emission layer may emit blue light having a central wavelength $\lambda_{max}$ of 430 nm to 490 nm.

The compound may be at least one among compounds represented in the following Compound Group 1:
[Compound Group 1]
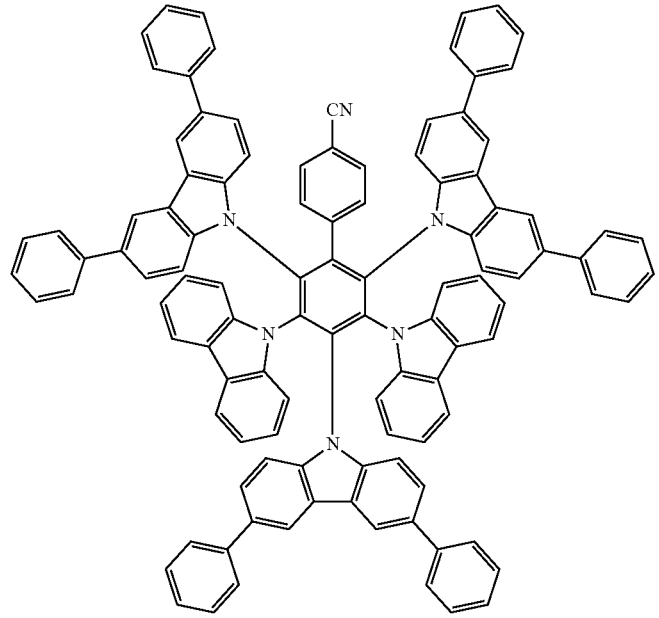
1
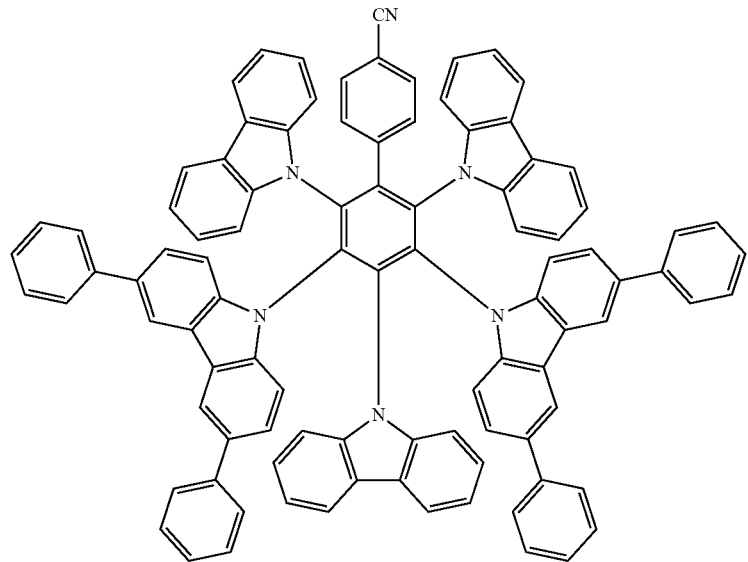
2

3
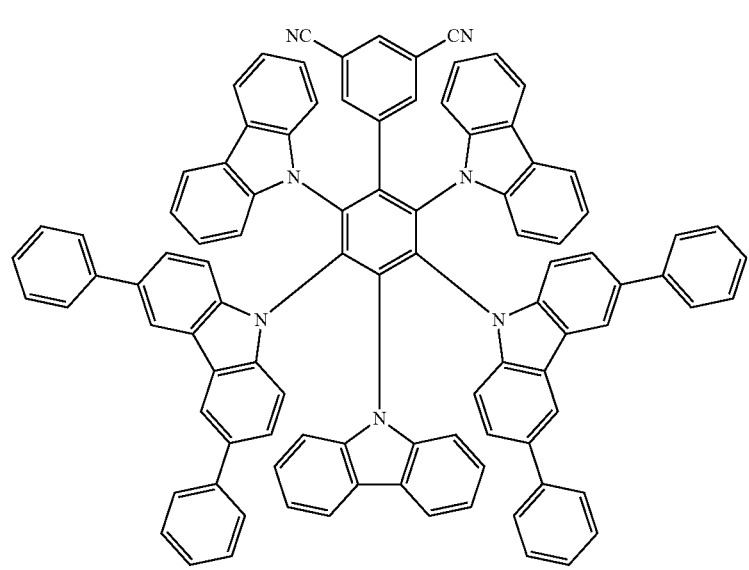
4
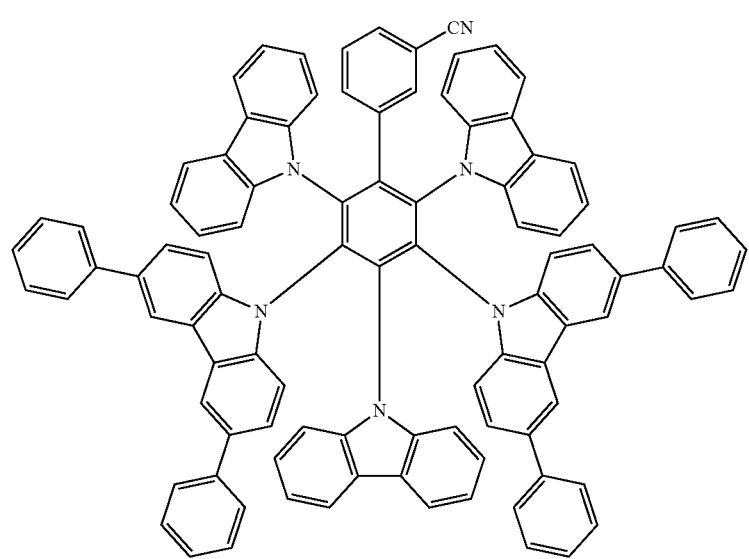

-continued
5
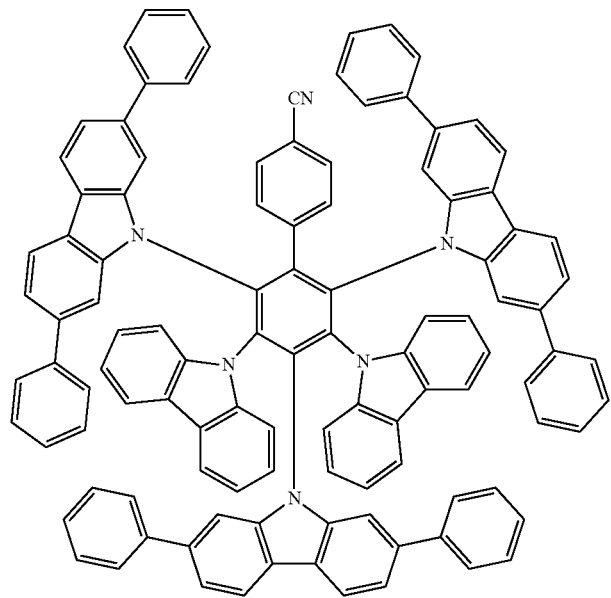
6
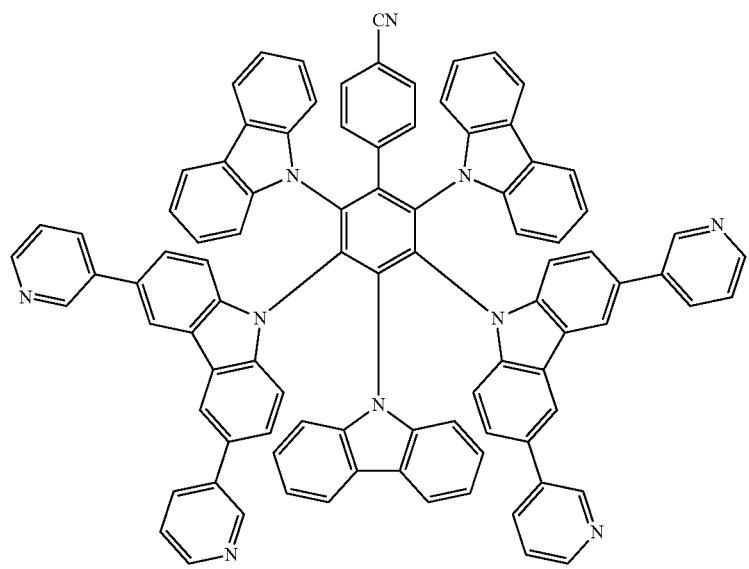

-continued
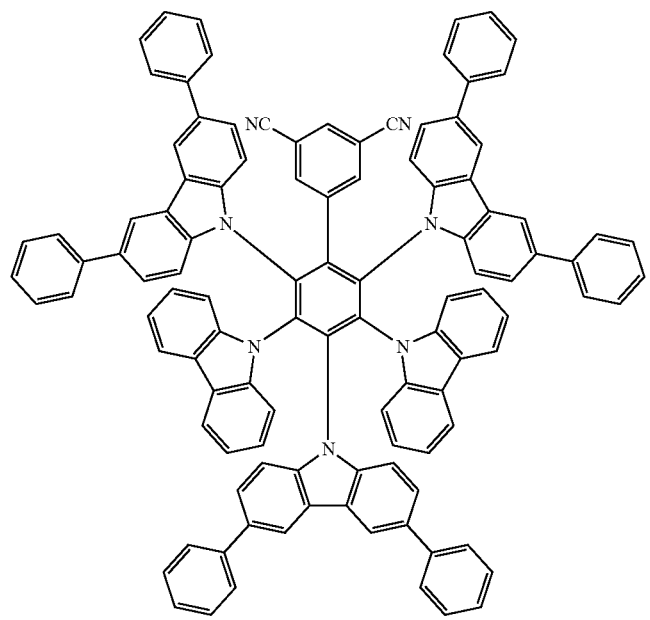
7
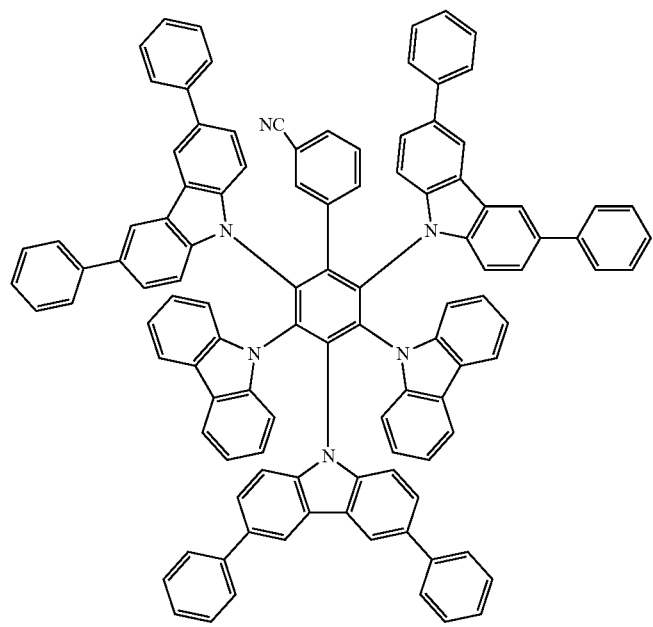
8

-continued
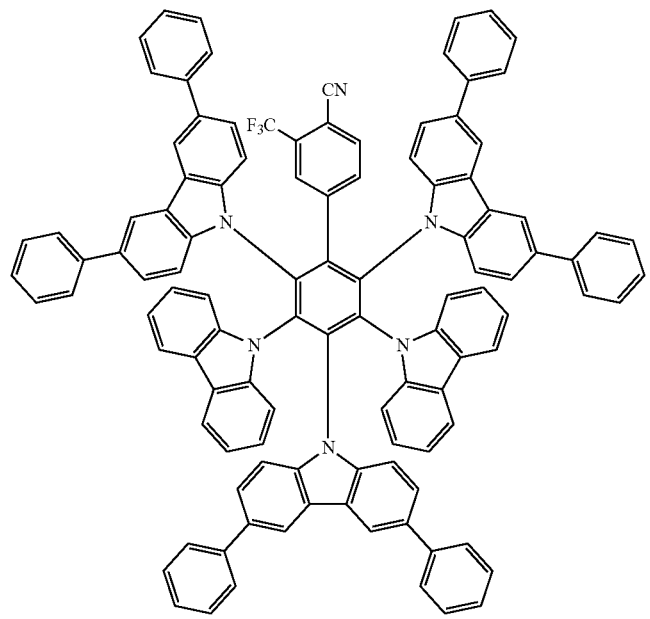
9
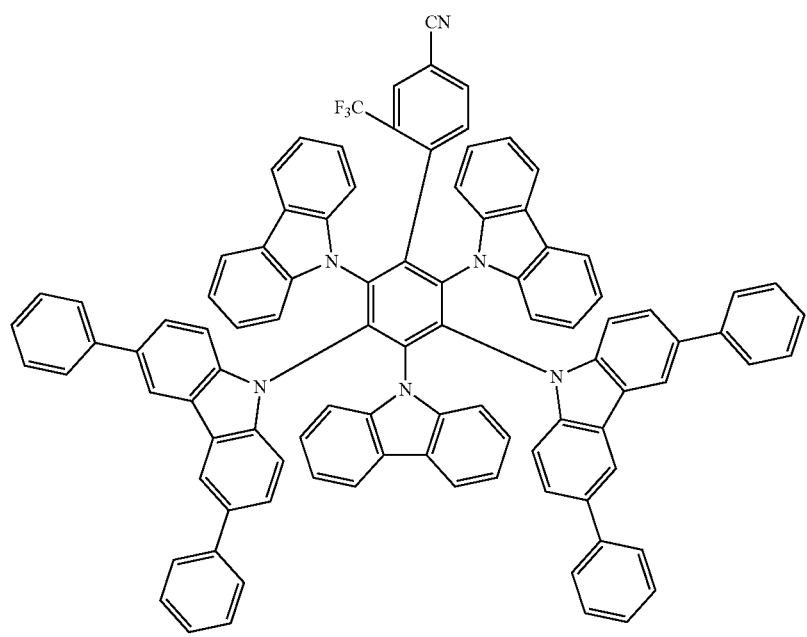
10

11

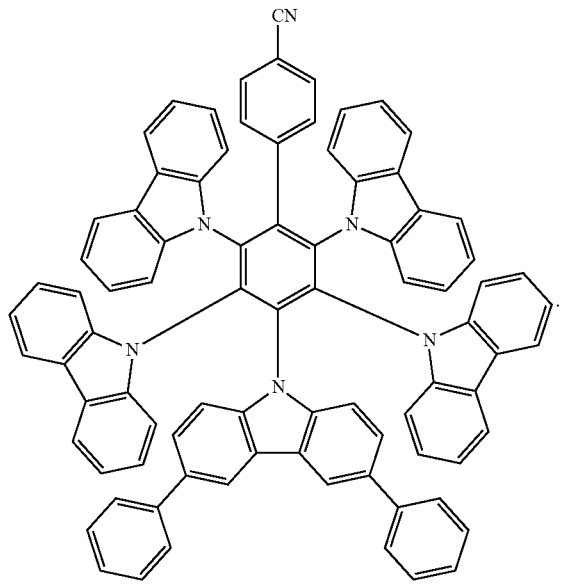

Embodiments are also directed to a compound represented by the following Formula 1:

[Formula 1]

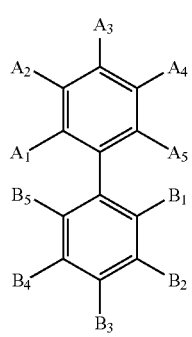

wherein, in Formula 1, at least one among $A_1$ to $A_5$ may be a cyano group, and the rest may each independently be a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, at least one among $B_1$ to $B_5$ may be represented by the following Formula 2-1 and the rest may each independently be represented by the following Formula 2-2:

[Formula 2-1]

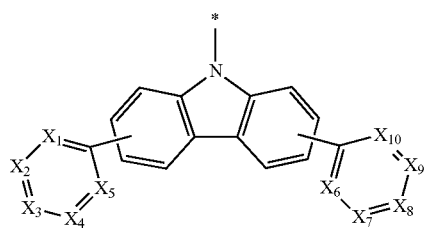

[Formula 2-2]

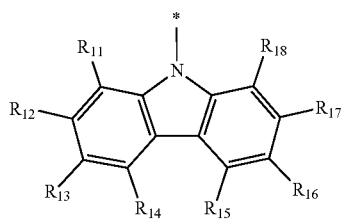

wherein, in Formula 2-1, $X_1$ to $X_{10}$ may each independently be N or $CR_1$, and $R_1$ may be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, wherein, in Formula 2-2, $R_{11}$ to $R_{18}$ may each independently be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms.

Formula 1 may be represented by any one among the following Formula 1-1 to Formula 1-3:
[Formula 1-1]
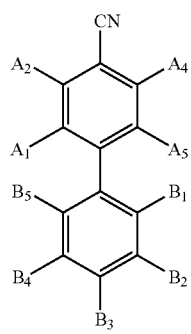
[Formula 1-2]
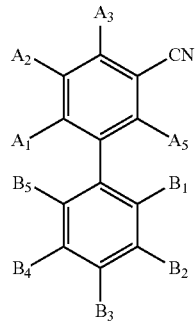
[Formula 1-3]
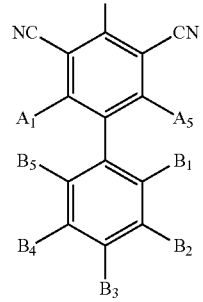
wherein, in Formula 1-1 to Formula 1-3, $A_1$ to $A_5$, and $B_1$ to $B_5$ are the same as defined in Formula 1.
Formula 1 may be represented by the following Formula 1-4 or Formula 1-5:
[Formula 1-4]
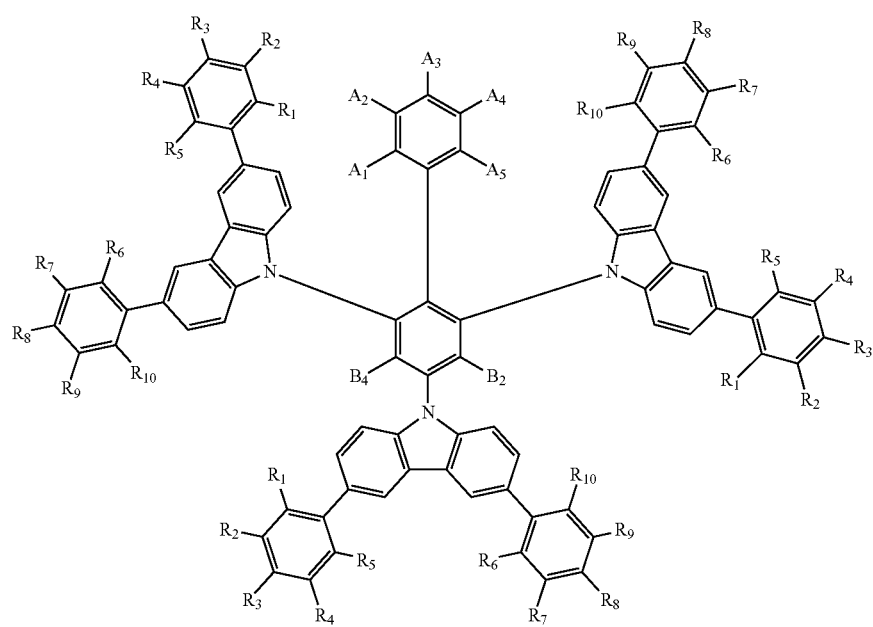

[Formula 1-5]
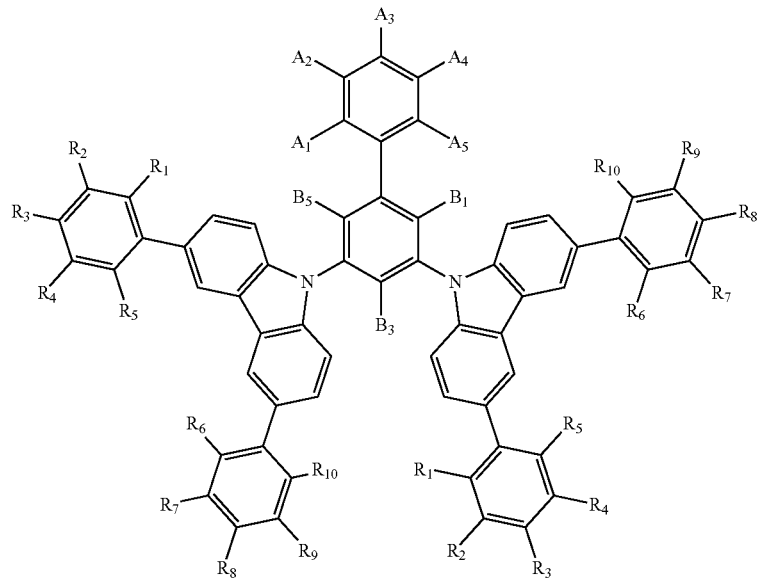
wherein,
in Formula 1-4, $B_2$ and $B_4$ may be represented by Formula 2-2,
in Formula 1-5, $B_1$, $B_3$, and $B_5$ may be represented by Formula 2-2, and
in Formula 1-4 and Formula 1-5, $A_1$ to $A_5$ are the same as defined in Formula 1.
Formula 2-1 may be represented by the following Formula 2-1A or Formula 2-1B, and Formula 2-2 may be represented by the following Formula 2-2A:
[Formula 2-1B]
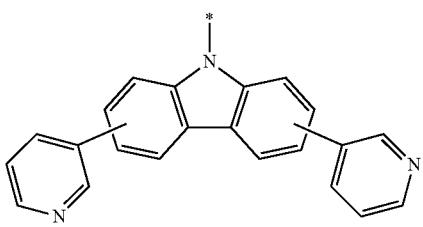
[Formula 2-1A]
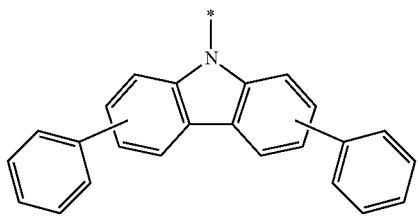
[Formula 2-2A]
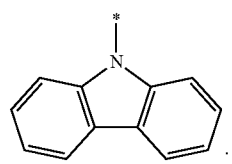

Formula 1 may be any one among compounds in the following Compound Group 1:
[Compound Group 1]
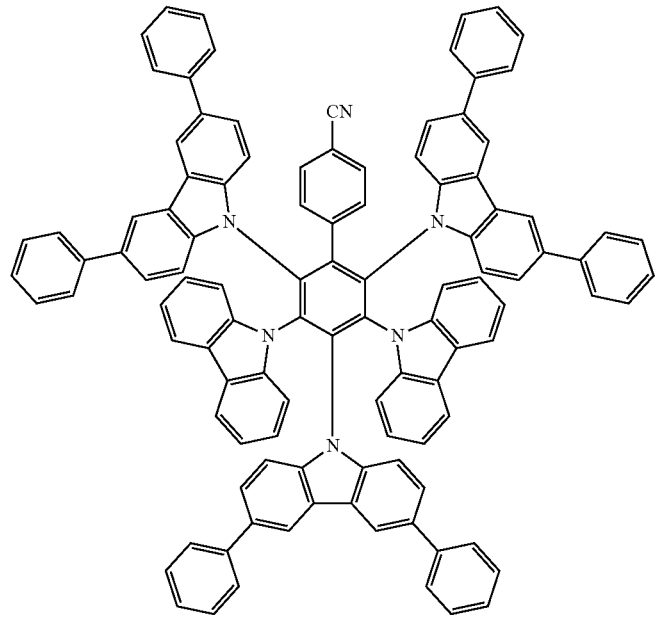
1
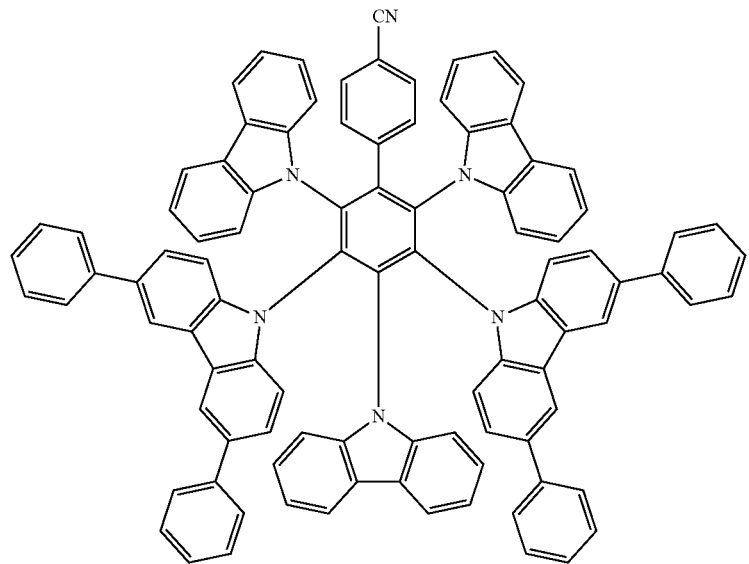
2

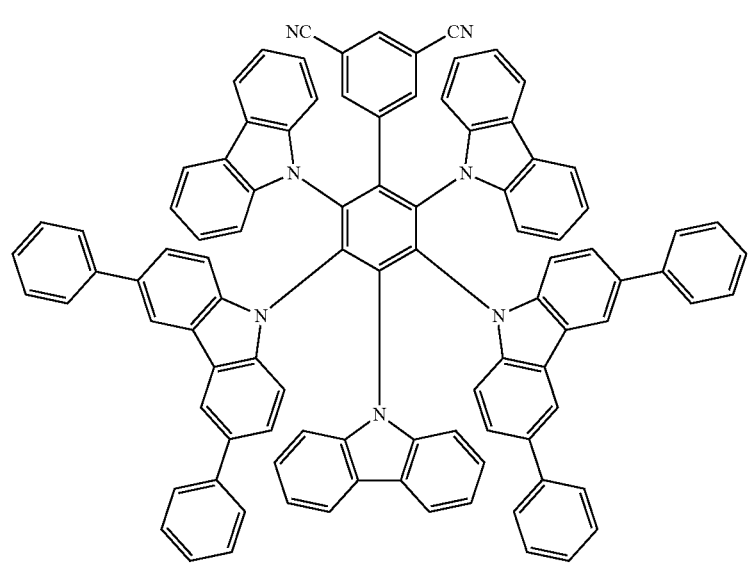
3
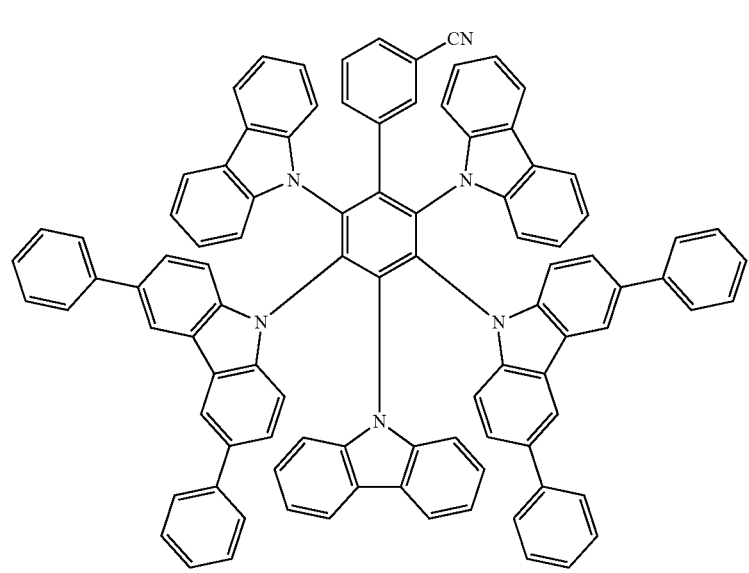
4

-continued
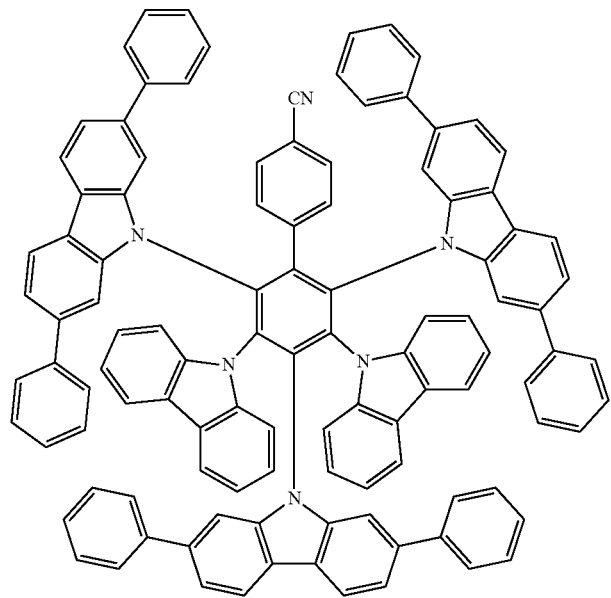
5
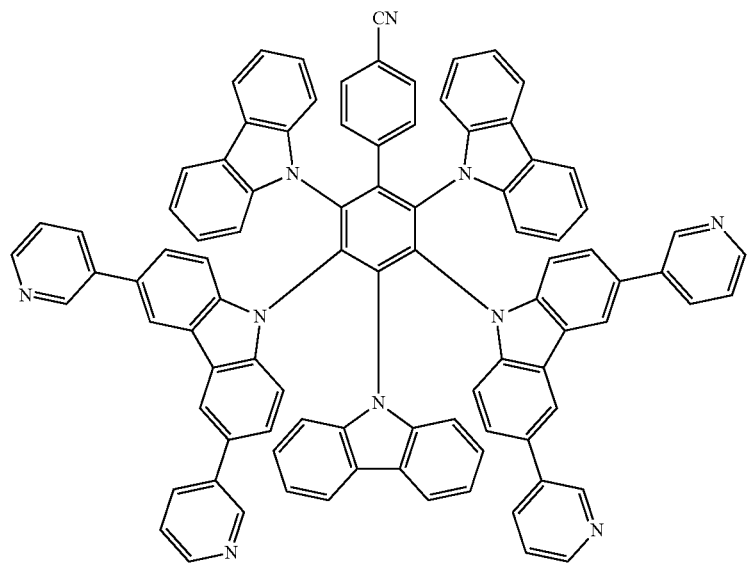
6

-continued
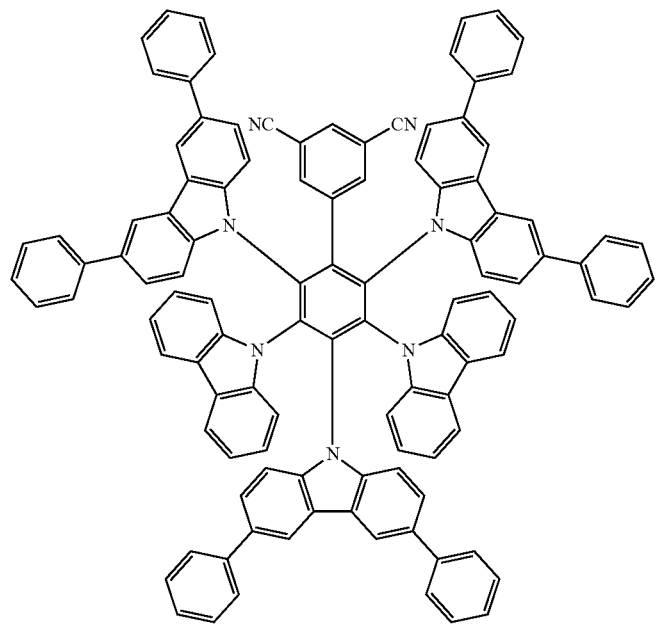
7
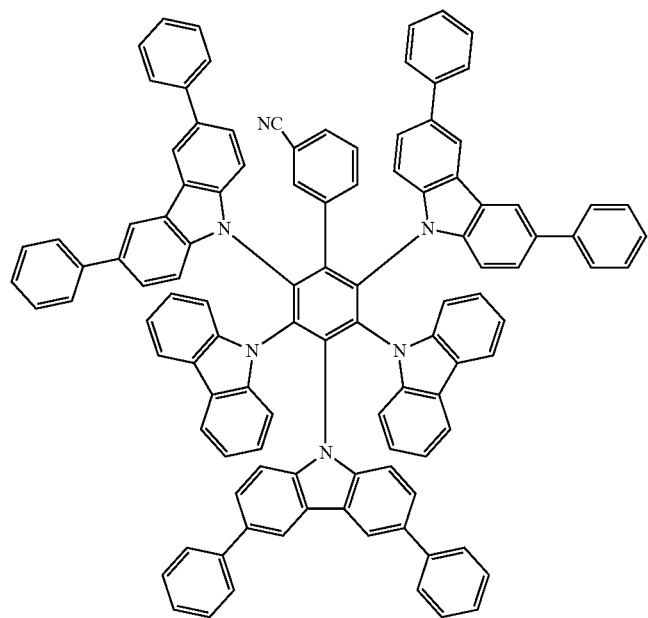
8

9
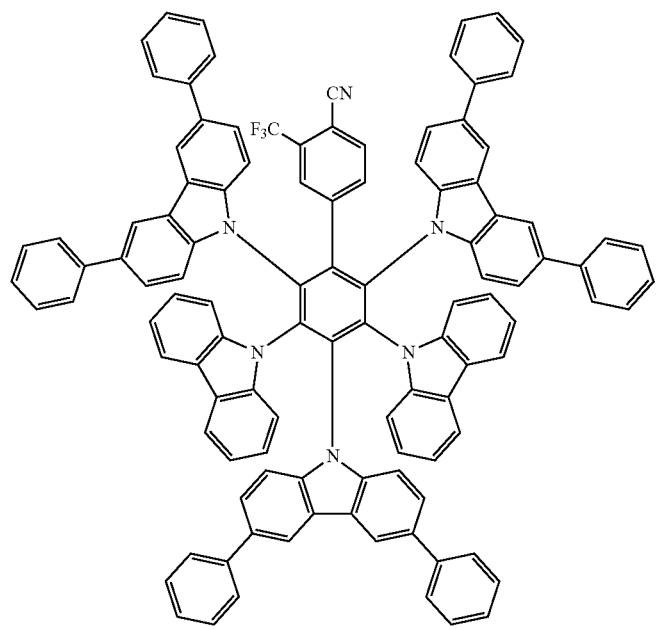
10
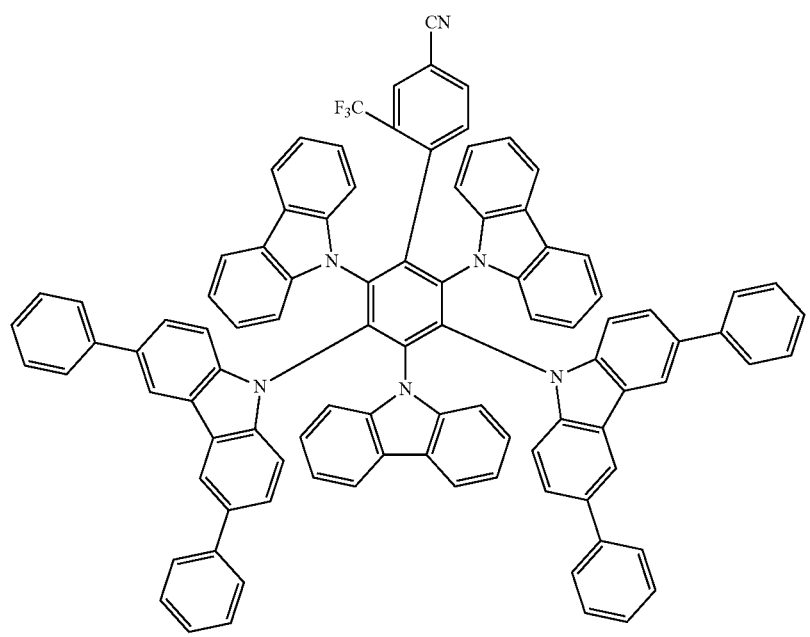

-continued

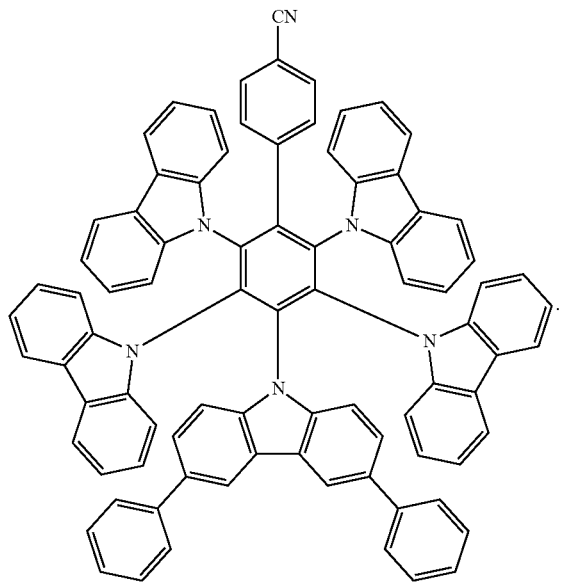

11

BRIEF DESCRIPTION OF THE DRAWINGS

Features will become apparent to those of skill in the art by describing in detail example embodiments with reference to the attached drawings in which.

DETAILED DESCRIPTION

Figure 1:
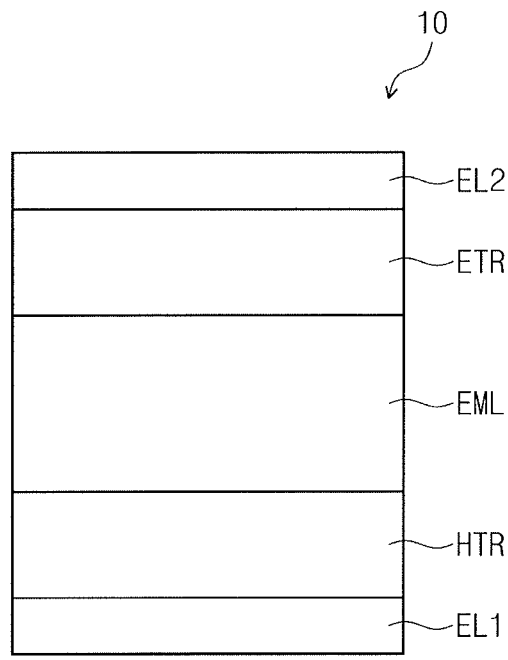
FIGS. 1 to 3 illustrate schematic cross-sectional views of organic electroluminescence devices according to example embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

It will be understood that when an element is referred to as being "on", "connected to" or "coupled to" another element, it can be directly on, connected or coupled to the other element or intervening elements may be present.

The term "and/or" includes one or more combinations which may be defined by relevant elements.

It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

In addition, the terms "below", "beneath", "on" and "above" are used for explaining the relation of elements shown in the drawings. The terms are relative concept and are explained on the basis of the direction shown in the drawing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

Hereinafter, an organic electroluminescence device according to an example embodiment will be explained with reference to attached drawings.

Figure 2:
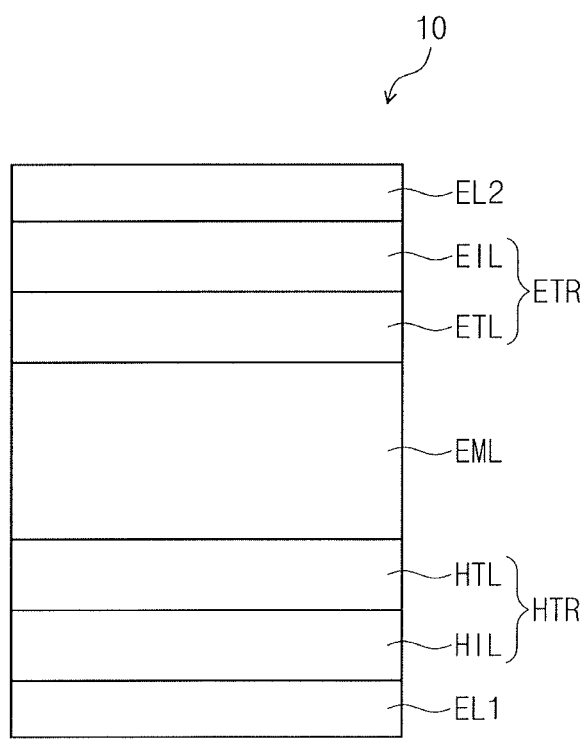
Figure 3:
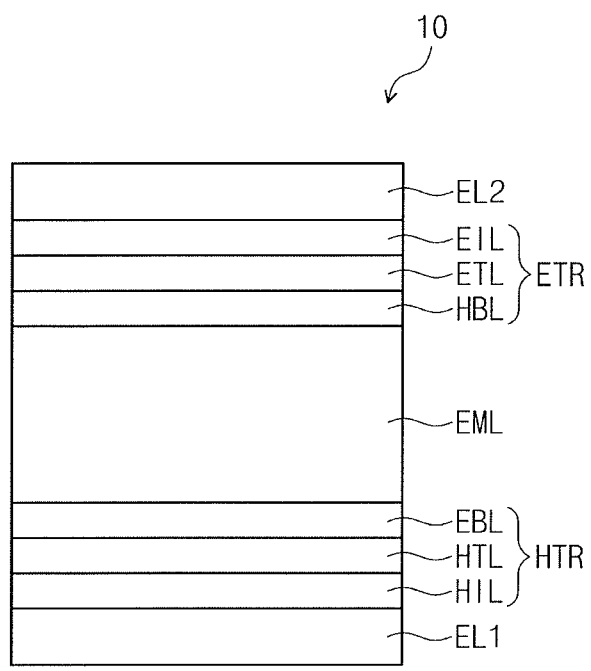

FIGS. 1 to 3 are cross-sectional views schematically showing organic electroluminescence devices according to example embodiments.

Referring to FIGS. 1 to 3, in an organic electroluminescence device 10 according to an example embodiment, a first electrode EL1 and a second electrode EL2 are oppositely disposed, and between the first electrode EL1 and the second electrode EL2, an emission layer EML may be disposed.

The organic electroluminescence device 10 according to the present example embodiment may include a plurality of organic layers in addition to the emission layer EML between the first electrode EL1 and the second electrode EL2. The plurality of the organic layers may include a hole transport region HTR and an electron transport region ETR. Thus, the organic electroluminescence device 10 according to the present example embodiment may include a first electrode EL1, a hole transport region HTR, an emission layer EML, an electron transport region ETR, and a second electrode EL2, laminated one by one.

The organic electroluminescence device 10 according to the present example embodiment may include a compound according to an example embodiment, which will be explained below, in the emission layer EML between the first electrode EL1 and the second electrode EL2. The organic electroluminescence device 10 according to the present example embodiment may include a compound according to an example embodiment, which will be explained below, in at least one organic layer among a plurality of organic layers between the first electrode EL1 and the second electrode EL2 in addition to the emission layer EML.

As compared with FIG. 1, FIG. 2 shows the cross-sectional view of an organic electroluminescence device 10 according to an example embodiment, wherein a hole transport region HTR includes a hole injection layer HIL and a hole transport layer HTL, and an electron transport region ETR includes an electron injection layer EIL and an electron transport layer ETL. In addition, when compared with FIG. 1, FIG. 3 shows the cross-sectional view of an organic electroluminescence device 10 according to the present example embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL.

The first electrode EL1 may have conductivity. The first electrode EL1 may be formed using a metal alloy or a conductive compound. The first electrode EL1 may be an anode. The first electrode EL1 may be a pixel electrode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. The thickness of the first electrode EL1 may be from about 1,000 Å to about 10,000 Å, for example, from about 1,000 Å to about 3,000 Å.

The hole transport region HTR may be provided on the first electrode EL1. The hole transport region HTR may include at least one of a hole injection layer HIL, a hole transport layer HTL, a hole buffer layer, or an electron blocking layer EBL. The thickness of the hole transport region HTR may be from about 50 Å to about 1,500 Å

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer of a hole injection layer HIL, or a hole transport layer HTL, and may have a structure of a single layer formed using a hole injection material and a hole transport material. In another implementation, the hole transport region HTR may have a structure of a single layer formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/ electron blocking layer EBL.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine, N,N'-diphenyl-N,N'-bis-[4-(phenyl-m-tolyl-amino)-phenyl]-phenyl-4,4'-diamine (DNTPD), 4,4',4"-[tris(3-methylphenyl)phenylamino]triphenylamine (m-MTDATA), 4,4', 4"-tris(N,N-diphenylamino)triphenylamine (TDATA), 4,4', 4"-tris {N,-2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], and dipyrazino[2,3-f:2', 3'-h]quinoxaline-2,3,6,7,10,11-hexacarbonitrile (HAT-CN).

The hole transport layer HTL may include, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 50 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 10 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds. For example, the p-dopant may include quinone derivatives such as tetracyanoquinodimethane (TCNQ) and 2,3,5,6-tetrafluoro-7,7',8,8'-tetracyanoquinodimethane (F4-TCNQ), metal oxides such as tungsten oxide, and molybdenum oxide.

As described above, the hole transport region HTR may further include at least one of a hole buffer layer or an electron blocking layer EBL in addition to the hole injection layer HIL and the hole transport layer HTL. The hole buffer layer may compensate an optical resonance distance according to the wavelength of light emitted from an emission layer EML and may increase light emission efficiency. Materials that may be included in a hole transport region HTR may be used as materials included in a hole buffer layer. The electron blocking layer EBL is a layer playing the role of preventing the electron injection from the electron transport region ETR to the hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed using a single material, a single layer formed using a plurality of different materials, or a multi-layer structure having a plurality of layers formed using a plurality of different materials.

In the organic electroluminescence device 10 according to the present example embodiment, the emission layer EML may include a compound according to an example embodiment, which may be a compound that includes a first phenyl group that is substituted with at least one cyano group, and a second phenyl group that is substituted with five substituted or unsubstituted carbazole groups, the second phenyl group being directly bonded to the first phenyl group.

In the compound according to the present example embodiment, the first phenyl group may include one or two cyano groups as substituents. In the first phenyl group, the remaining parts that are not substituted with the cyano group may be unsubstituted or substituted with a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms.

The at least one cyano group substituted in the first phenyl group may be substituted at a para position or a meta position with respect to the second phenyl group. For example, if the first phenyl group is substituted with one cyano group, the cyano group may be substituted at the para position or meta position with respect to the second phenyl group. In addition, for example, if the first phenyl group is substituted with two cyano groups, all two cyano groups may be substituted at the meta positions with respect to the second phenyl group.

In the compound according to the present example embodiment, the carbazole group that is substituted at the second phenyl group may be an unsubstituted carbazole group, a carbazole group that is substituted with an aryl group of 6 to 18 ring carbon atoms, or a carbazole group that is substituted with a heteroaryl group of 5 to 18 ring carbon atoms. For example, the carbazole group that is substituted in the second phenyl group may be an unsubstituted carbazole group, a carbazole group that is substituted with a phenyl group, or a carbazole group that is substituted with a pyridine group.

In the compound according to the present example embodiment, the second phenyl group may include at least one of a carbazole group that is substituted with an aryl group or a phenyl group that is substituted with a heteroaryl group. For example, the second phenyl group may include at least one carbazole group that is substituted with a phenyl group as a substituent, or at least one carbazole group that is substituted with a pyridine group as a substituent. In an example embodiment, the second phenyl group may include a plurality of carbazole groups that are substituted with phenyl groups as substituents, or a plurality of carbazole groups that are substituted with pyridine groups as substituents. The second phenyl group may include two or three carbazole groups that are substituted with phenyl groups as substituents. In another implementation, the second phenyl group may include two or three carbazole groups that are substituted with pyridine groups as substituents.

In addition, the remaining parts of the second phenyl group, which are unsubstituted with a carbazole group that is substituted with an aryl group or a carbazole group that is substituted with a heteroaryl group, may be substituted with unsubstituted carbazole groups. Thus, in the second phenyl group, all remaining parts (i.e., excluding a part that is bonded to the first phenyl group) may be substituted with substituted or unsubstituted carbazole groups.

In the carbazole group that is substituted with phenyl groups and that is substituted at the second phenyl group, the phenyl substituents in the carbazole group may be substituted in the benzene ring of the carbazole, respectively. The phenyl groups that are substituted in the benzene ring, respectively, may be substituted at symmetric positions to each other. In addition, in the carbazole group that is substituted with a pyridine group and that is substituted at the second phenyl group, the pyridine substituents of the carbazole group may be substituted in the benzene ring of the carbazole, respectively. The pyridine groups that are substituted in the benzene ring, respectively, may be substituted at symmetric positions to each other.

In the compound according to the present example embodiment, at least one cyano group that is substituted at the first phenyl group may be an electron acceptor, and the second phenyl group that is substituted with a substituted or unsubstituted carbazole group may be an electron donor.

The first phenyl group may be a linker connecting the cyano group substituent and the second phenyl group. The compound according to the present example embodiment may include the first phenyl group as a linker between the cyano group having electron accepting properties and the second phenyl group having electron donating properties, and may be used as a material for emitting blue light in a short wavelength region. Thus, the compound according to the present example embodiment may be used as a light-emitting material that emits deep blue light.

In the description, the term "substituted or unsubstituted" corresponds to substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group.

In the description, the halogen atom may be a fluorine atom, a chlorine atom, a bromine atom or an iodine atom.

In the description, the alkyl may be a linear, branched or cyclic type. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the description, the aryl group means an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc.

In the description, the heteroaryl may be a heteroaryl including at least one of O, N, P, Si or S as a heteroatom. If the heteroaryl includes two or more heteroatoms, two or more heteroatoms may be the same or different. The heteroaryl may be monocyclic heteroaryl or polycyclic heteroaryl. The carbon number for forming a ring of the heteroaryl may be 2 to 30, 2 to 20, or 2 to 10. Examples of the heteroaryl may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc.

In the description, "—*" means a connecting position.

The emission layer EML of the organic electroluminescence device 10 according to the present example embodiment may include a compound represented by the following Formula 1.

[Formula 1]

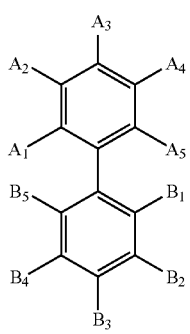

In Formula 1, at least one among $A_1$ to $A_5$ may be a cyano group, and the rest may each independently be a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms. Thus, in an implementation $A_1$ to $A_5$ may each independently be a cyano group, a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, provided that at least one among $A_1$ to $A_5$ is a cyano group.

In addition, at least one among $B_1$ to $B_5$ in Formula 1 may be represented by the following Formula 2-1 and the rest may be represented by the following Formula 2-2.

[Formula 2-1]

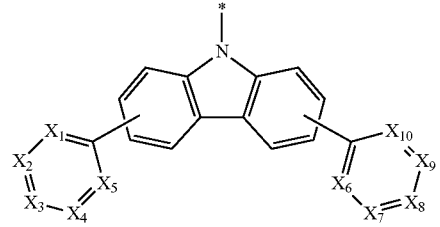

[Formula 2-2]

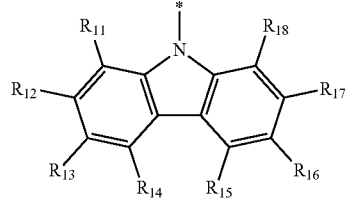

In Formula 1, the phenyl group in which $A_1$ to $A_5$ are substituted, i.e.,

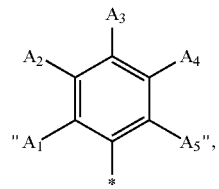

corresponds to the first phenyl group, and the phenyl group in which $B_1$ to $B_5$ are substituted, i.e.,

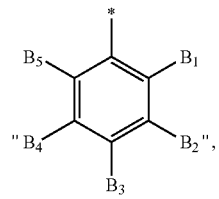

corresponds to the second phenyl group.

In Formula 2-1, $X_1$ to $X_{10}$ may each independently be N or $CR_1$, and $R_1$ may be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms. For example, in Formula 2-1, all $X_1$ to $X_{10}$ may be $CR_1$. In this case, all $R_1$ groups may be hydrogen atoms.

In addition, in Formula 2-1, any one among $X_1$ to $X_5$ and any one among $X_6$ to $X_{10}$ may be N. Any one selected among $X_1$ to $X_5$ and any one selected among $X_6$ to $X_{10}$ may be N and the rest may be $CR_1$. In this case, all $R_1$ groups may be hydrogen atoms.

In Formula 2-2, $R_{11}$ to $R_{18}$ may each independently be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms. For example, in the carbazole group represented by Formula 2-1 or Formula 2-2, all $R_1$, and $R_{11}$ to $R_{18}$ may be hydrogen atoms. Thus, Formula 2-1 may be represented by the following Formula 2-1A or Formula 2-1B, and Formula 2-2 may be represented by the following Formula 2-2A.

[Formula 2-1A]

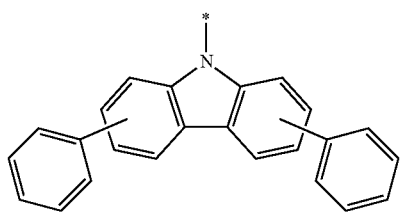

[Formula 2-1B]

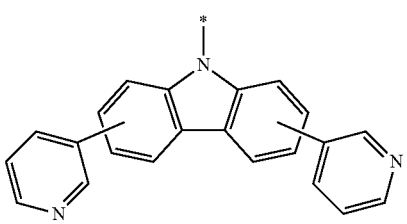

[Formula 2-2A]

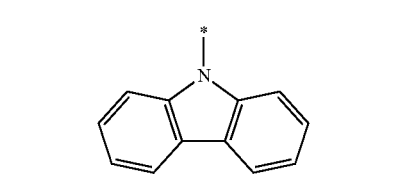

In an example embodiment, $R_1$, and $R_{11}$ to $R_{18}$ may each independently be a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms in addition to a hydrogen atom, and two or more selected from a plurality of $R_1$ groups or at least two selected among $R_{11}$ to $R_{18}$ may be the same or different.

Formula 2-1 may be represented by any one among the following Formula 3-1 to Formula 3-3.

[Formula 3-1]

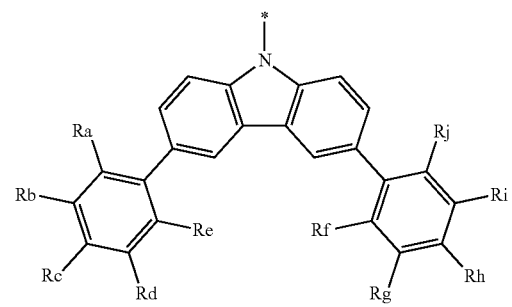

[Formula 3-2]

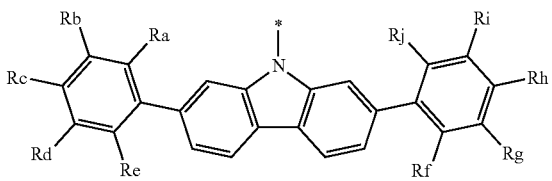

[Formula 3-3]

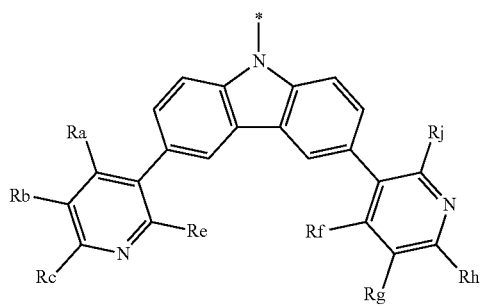

In Formula 3-1 to Formula 3-3, Ra to Rj may each independently be a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, and two or more selected among Ra to Rj may be the same or different. For example, Ra to Rj may be hydrogen atoms.

In Formula 1, one or two selected among $A_1$ to $A_5$ may be cyano groups. For example, Formula 1 may be represented by any one among the following Formula 1-1 to Formula 1-3.

[Formula 1-1]

[Formula 1-2]

[Formula 1-3]

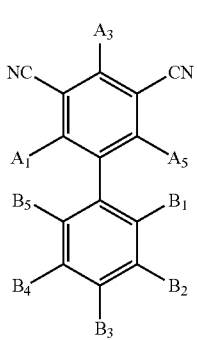

Formula 1-1 and Formula 1-2 correspond to cases where one cyano group is substituted in the first phenyl group, and Formula 1-3 corresponds to a case where two cyano groups are substituted in the first phenyl group.

Formula 1-1 represents a compound in which the substituted cyano group is substituted at a para position with respect to the second phenyl group, and Formula 1-2 represents a compound in which the substituted cyano group is substituted at a meta position with respect to the second phenyl group. In addition, Formula 1-3 represents a compound including two cyano groups as substituents, where two cyano groups are substituted at meta positions with respect to the second phenyl group.

In Formula 1-1 to Formula 1-3, the same explanation referring to Formula 1 may be applied to $A_1$ to $A_5$ and $B_1$ to $B_5$.

In Formula 1, two or three selected among $B_1$ to $B_5$ may be represented by Formula 2-1, and the rest may be represented by Formula 2-2. For example, Formula 1 may be represented by the following Formula 1-4 or Formula 1-5.

[Formula 1-4]

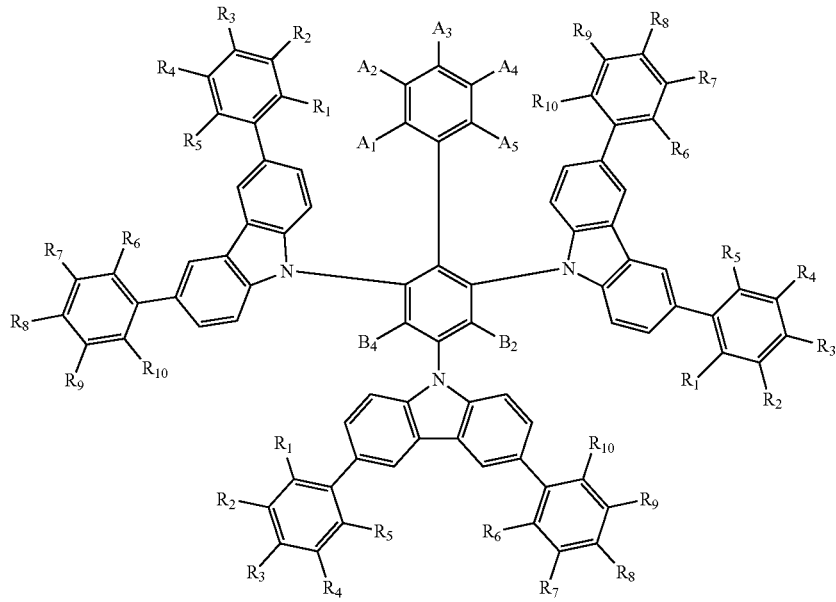

[Formula 1-5]

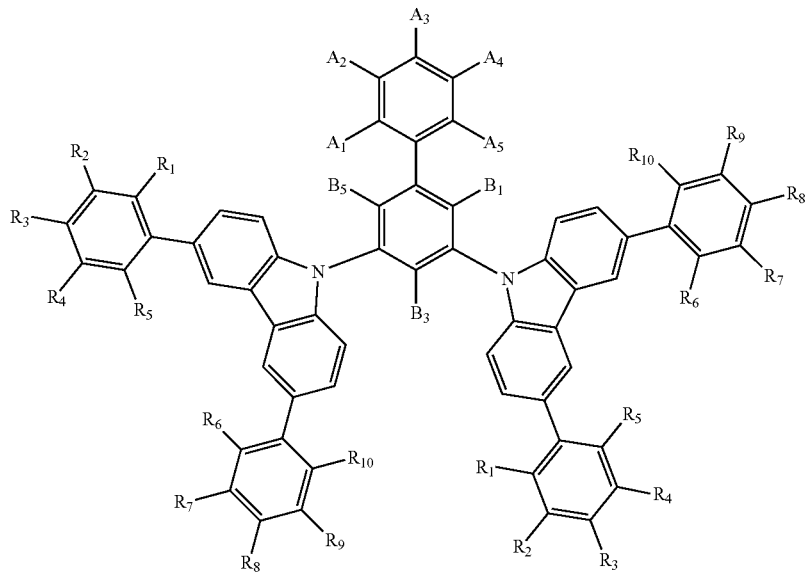

In Formula 1-4, $B_2$ and $B_4$ may be represented by Formula 2-2, and in Formula 1-5, $B_1$, $B_3$, and $B_5$ may be represented by Formula 2-2.

Formula 1-4 represents a case where the second phenyl group includes three substituted carbazole groups as substituents, and Formula 1-5 represents a case where the second phenyl group includes two substituted carbazole groups as substituents.

In Formula 1-4 and Formula 1-5, the same explanation referring to Formula 1 may be applied to $A_1$ to $A_5$.

The compound according to the present example embodiment may be any one among the compounds represented in the following Compound Group 1.

[Compound Group 1]

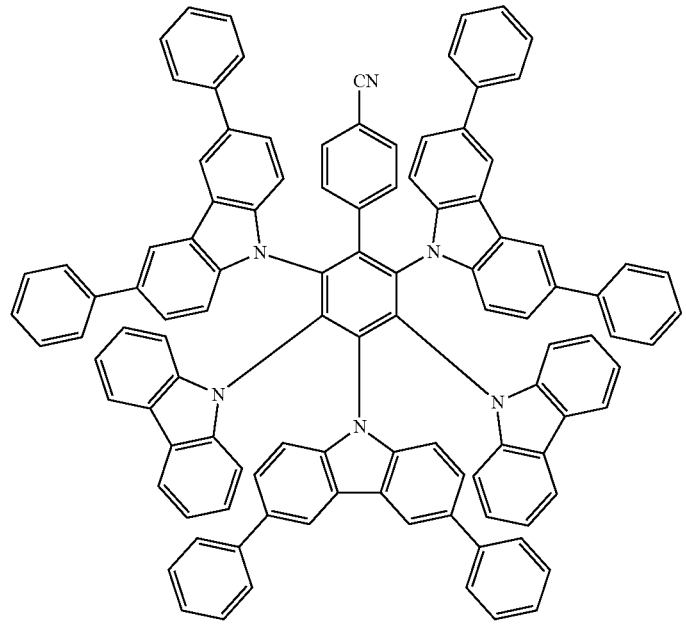

1

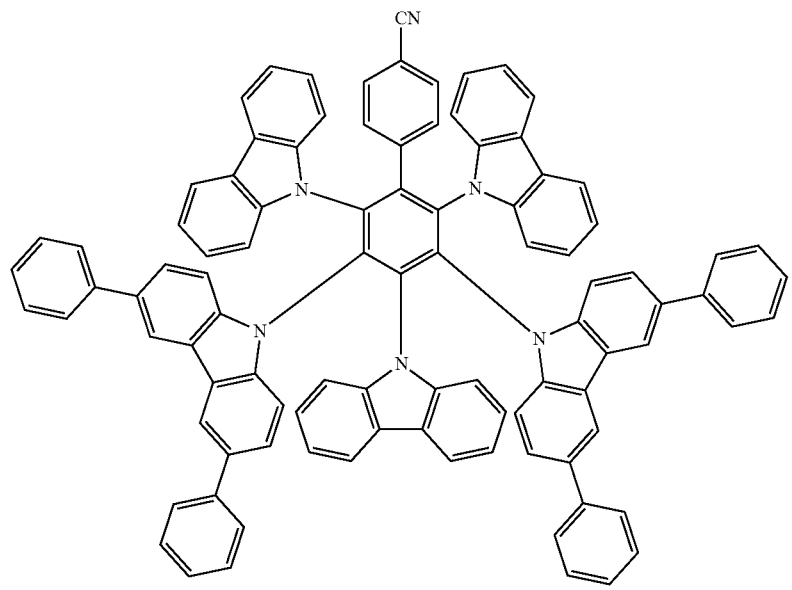

2

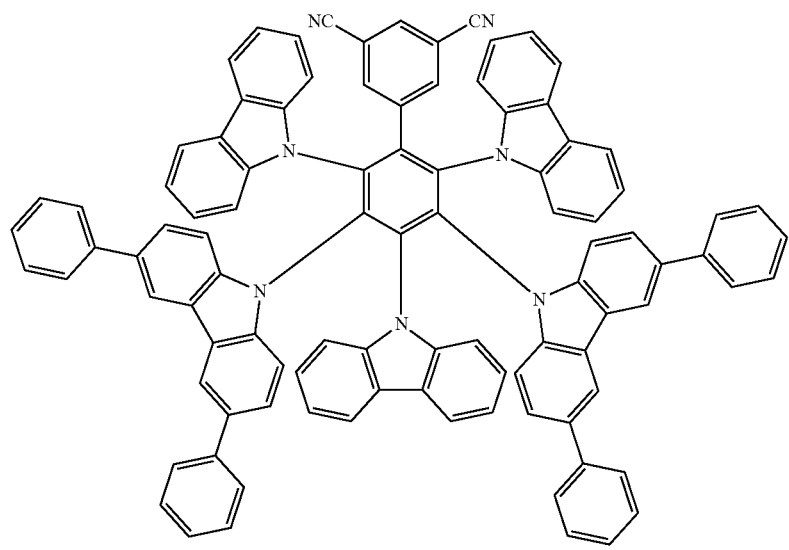
3
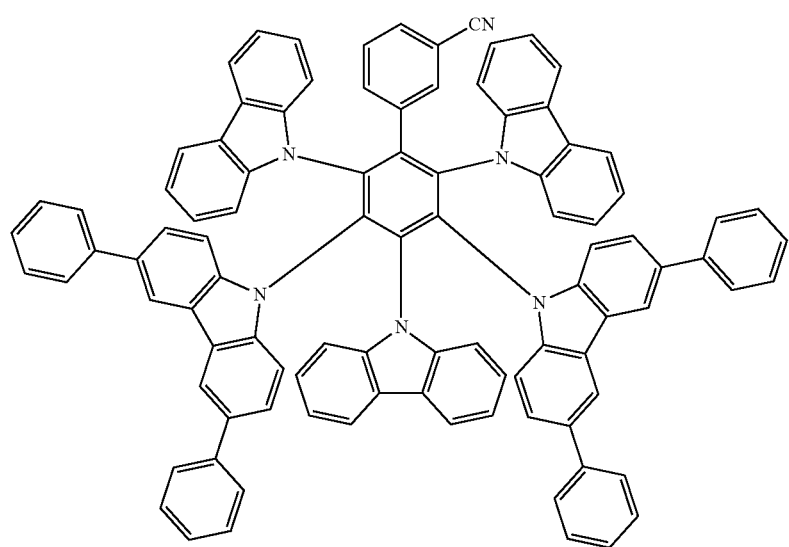
4

-continued
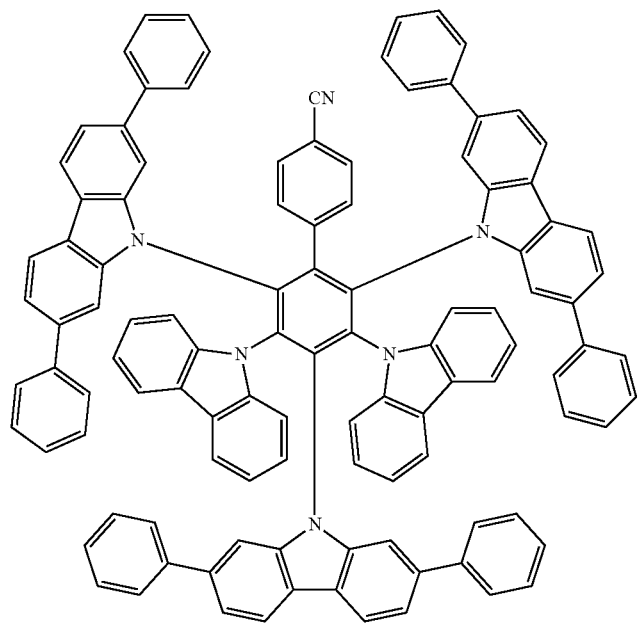
5
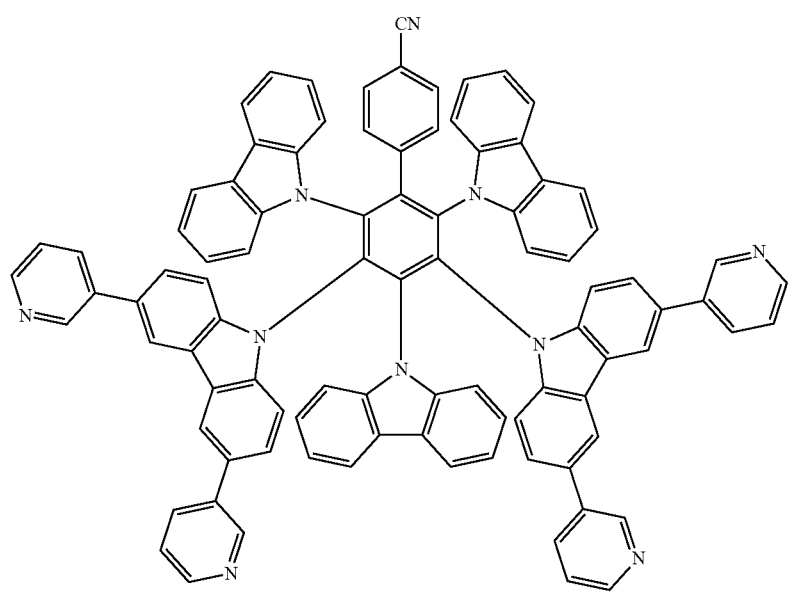
6

-continued
7
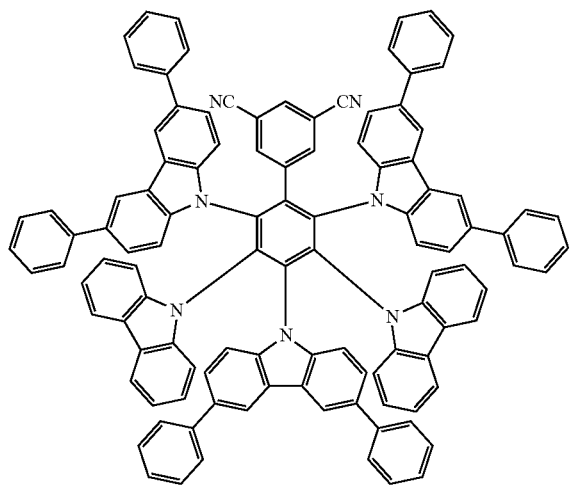
8
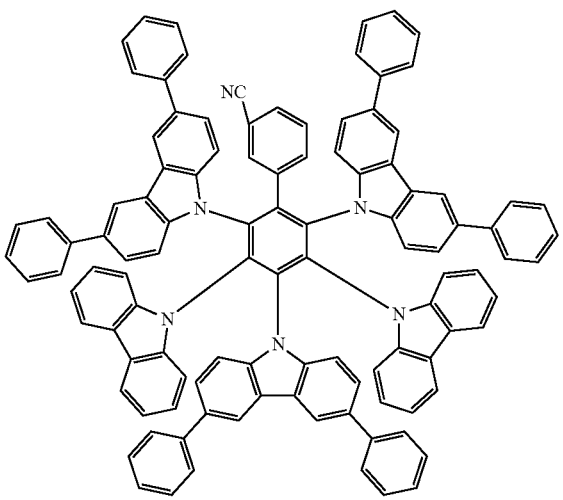
9
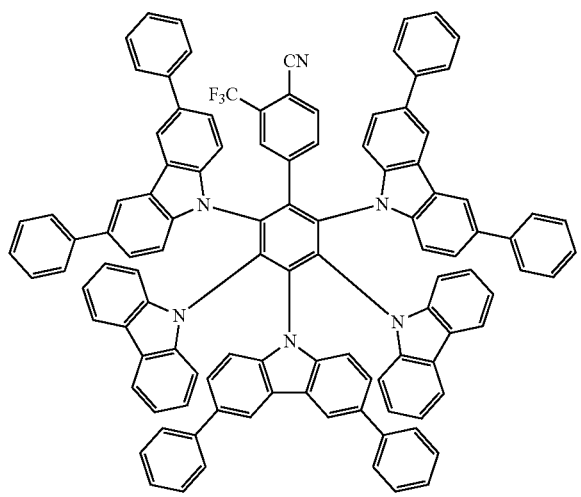
10
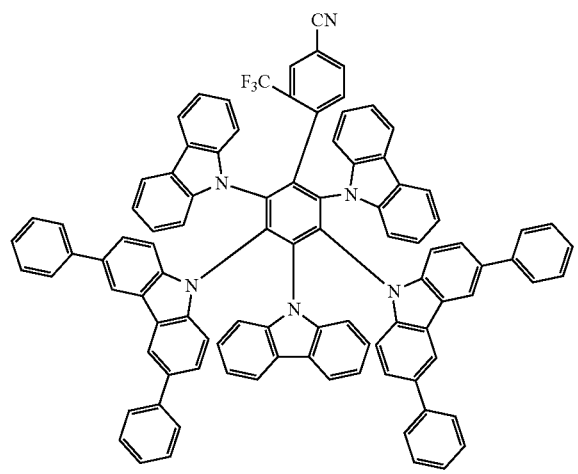
11
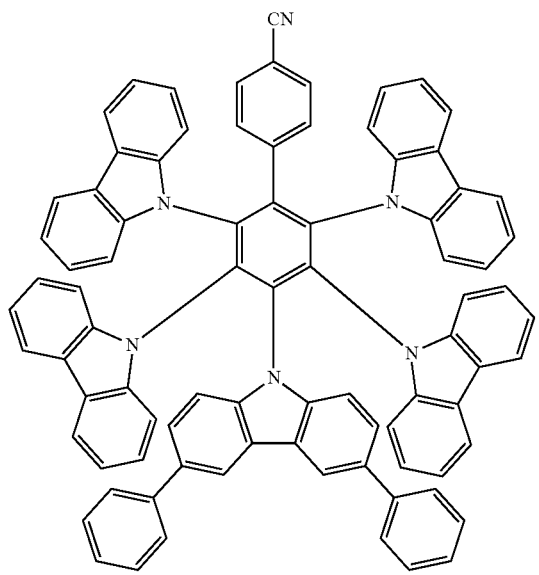

In an example embodiment, the organic electroluminescence device 10 may include at least one compound among the compounds represented in Compound Group 1 in the emission layer EML.

According to an example embodiment, the compound represented by Formula 1 may be a material for emitting light by thermally activated delayed fluorescence. In an example embodiment, the compound represented by Formula 1 may be a thermally activated delayed fluorescence dopant having an energy difference $\Delta E_{ST}$ between the lowest triplet excitation energy level (T1 level) and the lowest singlet excitation energy level (S1 level) of about 0.25 eV or less.

According to an example embodiment, the compound represented by Formula 1 may be a light-emitting material having a light-emitting central wavelength ($\lambda_{max}$) in a wavelength region of about 490 nm or less. For example, the compound according to the present example embodiment, represented by Formula 1 may be a light-emitting material having light-emitting central wavelength $\lambda_{max}$ in a wavelength region of about 430 nm to about 490 nm. According to an example embodiment, the compound represented by Formula 1 may be a deep blue thermally activated delayed fluorescence dopant.

In the organic electroluminescence device 10 according to the present example embodiment, the emission layer EML may emit light by delayed fluorescence. For example, the emission layer EML may emit light by thermally activated delayed fluorescence (TADF).

The organic electroluminescence device 10 according to an example embodiment may include a plurality of emission layers. The plurality of emission layers may be laminated one by one. For example, the organic electroluminescence device 10 including a plurality of emission layers may emit white light. The organic electroluminescence device including a plurality of emission layers may be an organic electroluminescence device having a tandem structure. If the organic electroluminescence device 10 includes a plurality of emission layers, at least one emission layer EML may include the compound according to the present example embodiment.

In an example embodiment, the emission layer EML includes a host and a dopant, and may include the compound according to an example embodiment as a dopant. For example, in the organic electroluminescence device 10 according to an example embodiment, the emission layer EML may include a host for emitting light by delayed fluorescence and a dopant for emitting light by delayed fluorescence, and may include the compound according to an example embodiment as a dopant for emitting delayed fluorescence. The emission layer EML may include at least one among the compounds represented in Compound Group 1 as a thermally activated delayed fluorescence dopant.

In an example embodiment, the emission layer EML may be a delayed fluorescence emission layer, and the emission layer EML may include a suitable host material and the compound according to the present example embodiment. For example, in an embodiment, the compound may be used as a TADF dopant.

In an example embodiment, the emission layer EML may include a suitable host material. For example, in an example embodiment, the emission layer EML may include, as a host material, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), 3,3'-bis(N-carbazolyl)-1,1'-biphenyl (mCBP), 1,3-bis(N-carbazolyl) benzene (mCP), etc. Suitable host materials for emitting delayed fluorescence other than the noted host materials may be included.

In the organic electroluminescence device 10 according to an example embodiment, the emission layer EML may further include a suitable dopant material. In an example embodiment, the emission layer EML may include, as a dopant, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

In the organic electroluminescence device 10 according to example embodiments, as shown in FIGS. 1 to 3, the electron transport region ETR may be provided on the emission layer EML. The electron transport region ETR may include at least one of a hole blocking layer HBL, an electron transport layer ETL or an electron injection layer EIL.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure laminated from the emission layer EML of electron transport layer ETL/electron injection layer EIL, or hole blocking layer HBL/electron transport layer ETL/electron injection layer EIL. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include an anthracene-based compound. The electron transport region may include, for example, tris(8-hydroxyquinolinato)aluminum ($Alq_3$), 1,3,5-tri[(3-pyridyl)-phen-3-yl] benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d] imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4- tert-butylphenyl)-1,3,4-oxadiazole (tBu-PBD), bis(2-methyl-8-quinolinolato-N1,08)-(1,1'-biphenyl-4-olato) aluminum (BAlq), berylliumbis(benzoquinolin-10-olate (Bebq2), 9,10-di(naphthalene-2-yl)anthracene (ADN), or a mixture thereof. The thickness of the electron transport layer ETL may be from about 100 Å to about 1,000 Å and may be, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may include, for example, LiF, 8-hydroxyquinolinolato-lithium (LiQ), Li$_2$O, BaO, NaCl, CsF, a metal in lanthanides such as Yb, or a metal halide such as RbCl, RbI and KI. The electron injection layer EIL also may be formed using a mixture material of an electron transport material and an insulating organometal salt. The organometal salt may be a material having an energy band gap of about 4 eV or more. Particularly, the organometal salt may include, for example, metal acetates, metal benzoates, metal acetoacetates, metal acetylacetonates, or metal stearates. The thickness of the electron injection layer EIL may be from about 1 Å to about 100 Å, and from about 3 Å to about 90 Å. If the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen).

The second electrode EL2 may be provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The second electrode EL2 may be connected with an auxiliary electrode. If the second electrode EL2 is connected with the auxiliary electrode, the resistance of the second electrode EL2 may be decreased.

On the second electrode EL2 of the organic electroluminescence device 10, a capping layer may be further disposed. The capping layer may include, for example, α-NPD, NPB, TPD, m-MTDATA, Alq$_3$, CuPc, N4,N4,N4',N4'-tetra (biphenyl-4-yl) biphenyl-4,4'-diamine (TPD15), 4,4',4"-tris (carbazol sol-9-yl) triphenylamine (TCTA), N,N'-bis(naphthalene-1-yl), etc.

The organic electroluminescence device 10 according to an example embodiment includes the compound according to the present example embodiment in the emission layer EML between the first electrode EL1 and the second electrode EL2, thereby showing excellent life characteristics and emitting blue light in a short wavelength region. In addition, the compound according to an example embodiment may be a thermally activated delayed fluorescence dopant, and the emission layer EML may include the compound according to an example embodiment to emit light by thermally activated delayed fluorescence. Accordingly, excellent emission efficiency properties may be achieved while emitting blue light in a short wavelength.

The compound according to the present example embodiment may be included in an organic layer other than the emission layer EML as a material for the organic electroluminescence device 10. For example, the organic electroluminescence device 10 according to an example embodiment may include the compound in at least one organic layer between the first electrode EL1 and the second electrode EL2, or in a capping layer on the second electrode EL2.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

1. Synthesis of Compounds of According to Example Embodiments

Example synthetic methods of polycyclic compounds according to example embodiments will now be explained referring to the synthetic methods of Compound 1 to Compound 4.

(Synthetic method of Compound 1)
<Synthesis of Intermediate A-1>

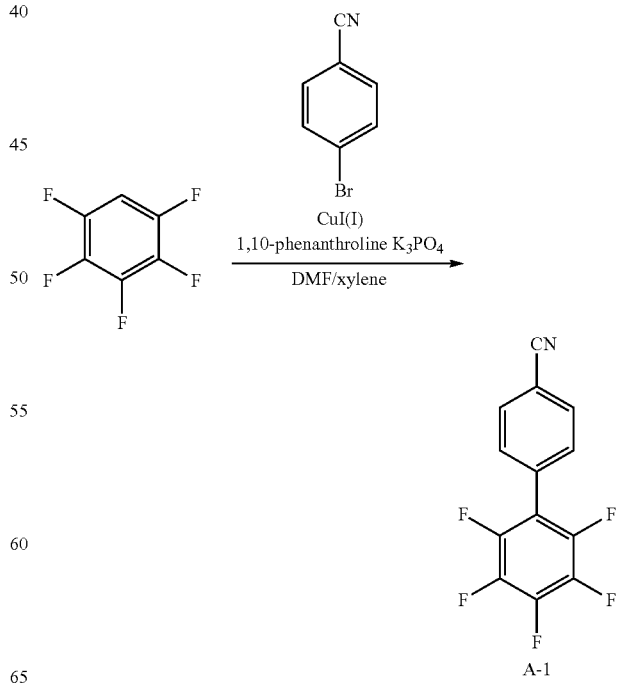

A-1

To a three-necked flask, 10 g (55 mmol) of 4-bromobenzonitrile, 9.2 g (55 mmol) of pentafluorobenzene, 1.0 g (5.5 mmol) of CuI, 1.0 g (5.5 mmol) of phenanthroline, and 23 g (110 mmol) of K$_3$PO$_4$ were added, and argon (Ar) flush was performed. Then, 16 ml of DMF and 16 ml of xylene were added thereto followed by heating and stirring at about 130° C. for about 24 hours. The reaction solution thus obtained was extracted with ethyl acetate, washed with brine, dried with magnesium sulfate, filtered using a silica gel pad and separated by silica gel column chromatography (mixed solvent of hexane/ethyl acetate) to obtain 9.6 g (yield 65%) of a white solid. The molecular weight of the separated product thus obtained was determined to be 269 by FAB-MS measurement, and the production of Intermediate A-1 which was a target material was confirmed.

<Synthesis of Intermediate A-2>

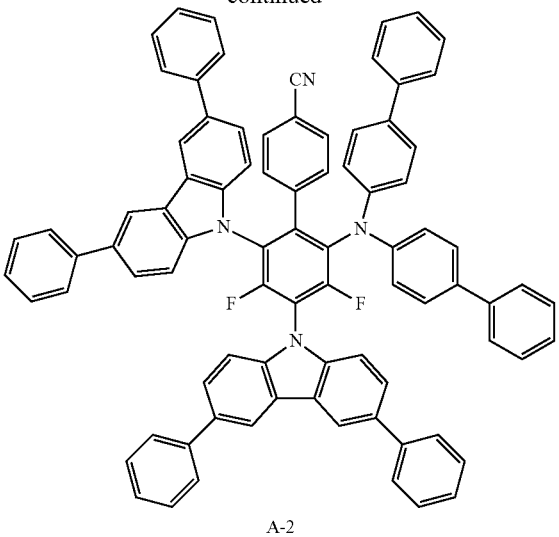

A-2

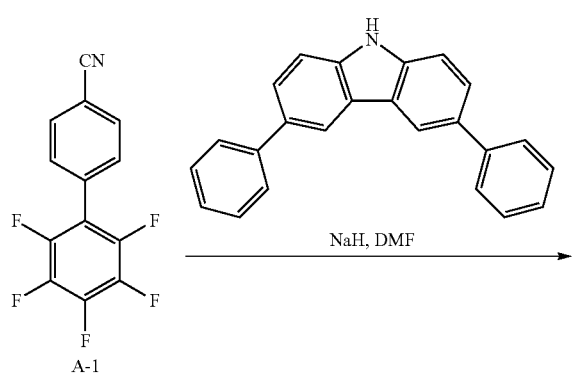

To a three-necked flask, 1.0 g (3.7 mmol) of Intermediate A-1, 4.2 g (13 mmol) of 3,6-diphenyl carbazole, and 0.22 g (9.3 mmol) of NaH were added, and argon flush was performed. 60 ml of DMF was added thereto, followed by stirring at about 0° C. for about 30 minutes. Then, the temperature of the reaction system was elevated to room temperature, and the reaction system was stirred for about 6 hours. Water was added to the reaction system, and an organic layer was extracted using dichloromethane and dried with MgSO$_4$. Then, solvents were removed by distillation. The crude product thus obtained was separated by silica gel column chromatography (mixed solvent of hexane/toluene) and using a recrystallization solvent (mixed solvent of ethanol/toluene) to obtain 0.79 g (yield 30%) of a pale yellow solid. The molecular weight of the separated product thus obtained was found to be 1167 by FAB-MS measurement, and the production of Intermediate A-2 which was a target material was confirmed.

<Synthesis of Compound 1>

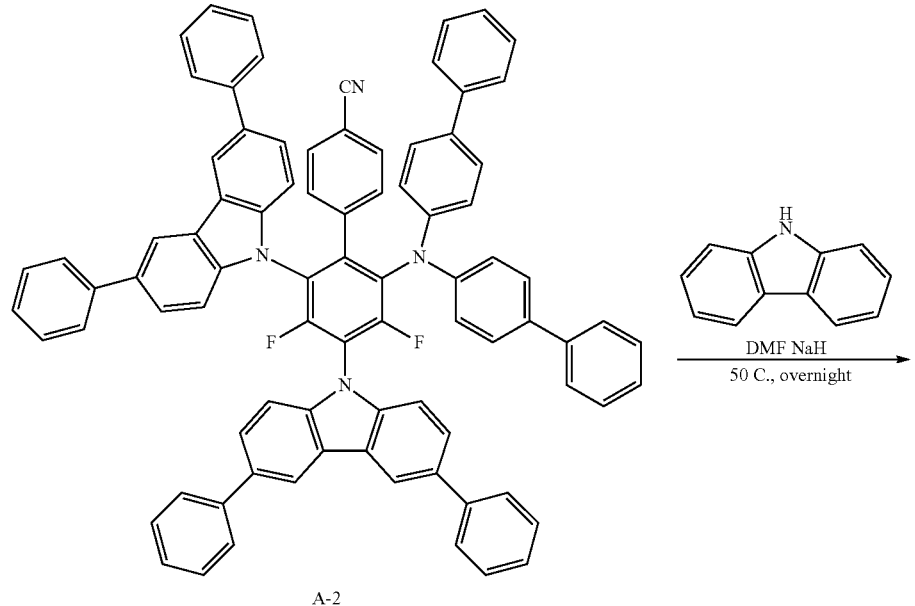

A-2

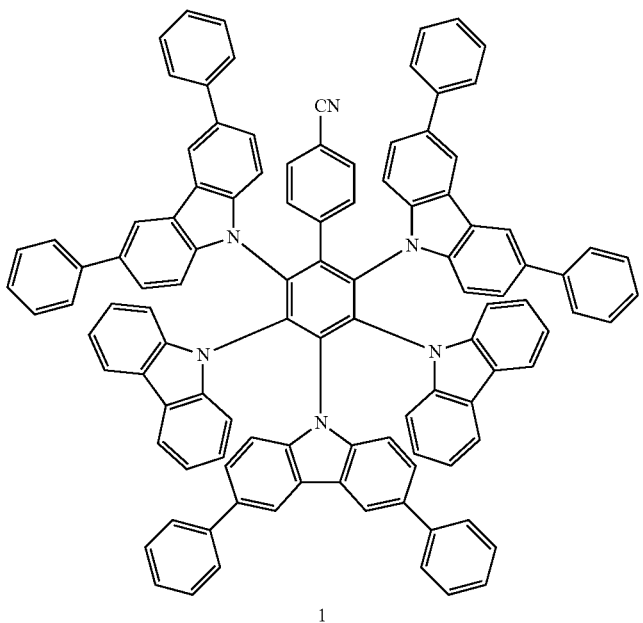

1

To a three-necked flask, 0.67 g (0.97 mmol) of Intermediate A-2, 0.30 g (1.9 mmol) of carbazole, and 0.57 g (2.3 mmol) of NaH were added, and argon flush was performed. 60 ml of DMF was added thereto, followed by stirring at about 0° C. for about 30 minutes. Then, the temperature of the reaction system was elevated to room temperature, and the reaction system was stirred for about 6 hours. Water was added to the reaction system, and an organic layer was extracted using dichloromethane and dried with MgSO$_4$. Then, solvents were removed by distillation. The crude product thus obtained was separated by silica gel column chromatography (mixed solvent of hexane/toluene) and using a recrystallization solvent (mixed solvent of ethanol/toluene) to obtain 0.74 g (yield 60%) of a pale yellow solid. The molecular weight of the separated product thus obtained was found to be 1448 by FAB-MS measurement, and the production of Compound 1 was confirmed.

(Synthetic Example of Compound 2)

<Synthesis of Intermediate A-3>

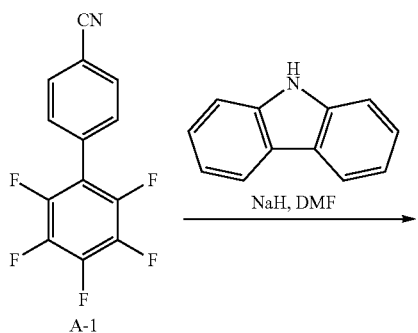

A-1

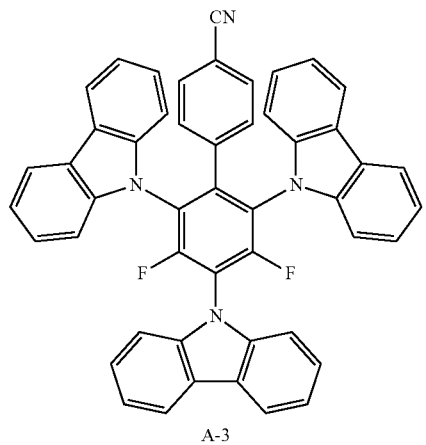

A-3

Intermediate A-3 was synthesized by performing the same procedure as in the synthetic method of Intermediate A-2 except for using carbazole instead of 3,6-diphenyl carbazole. 0.42 g (yield 16%) of a pale yellow solid was obtained. The molecular weight of the separated product thus obtained was found to be 711 by FAB-MS measurement, and the production of Intermediate A-3 which was a target material, was confirmed.

<Synthesis of Compound 2>

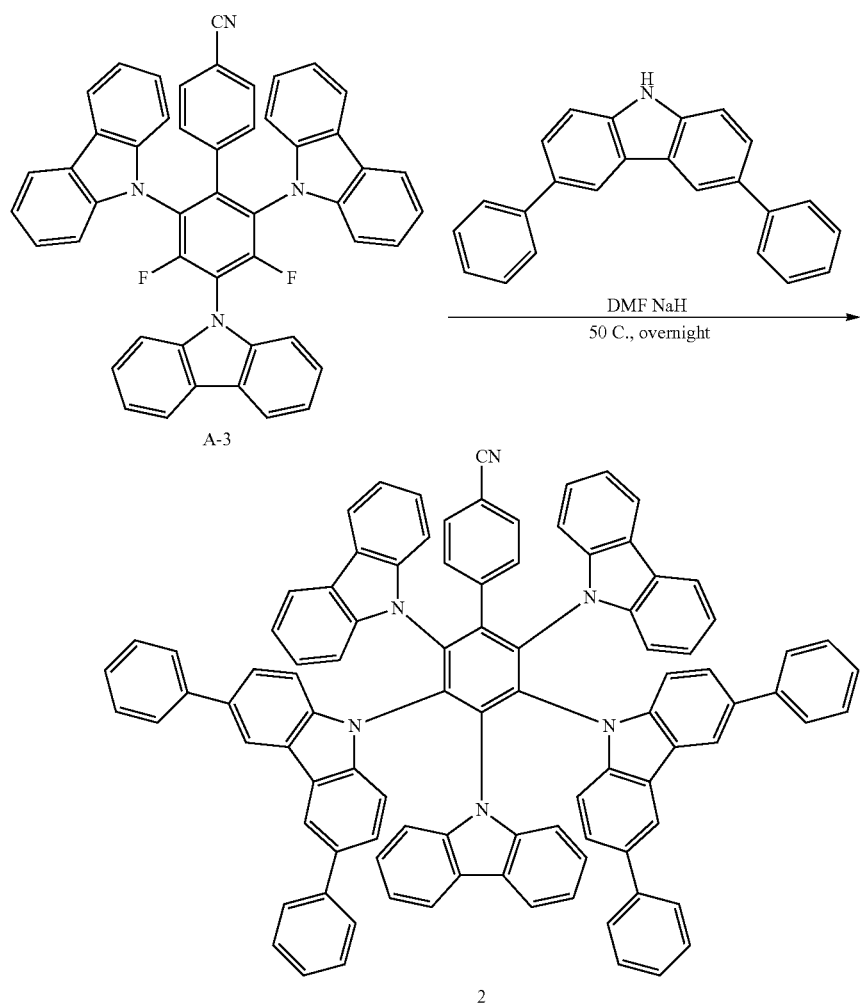

Compound 2 was synthesized by performing the same procedure as in the synthetic method of Compound 1 except for using 3,6-diphenyl carbazole instead of carbazole. 0.43 g (yield 70%) of a pale yellow solid was obtained. The molecular weight of the separated product thus obtained was found to be 1310 by FAB-MS measurement, and the production of Compound 2 was confirmed.

(Synthetic Example of Compound 3)

<Synthesis of Intermediate B-1>

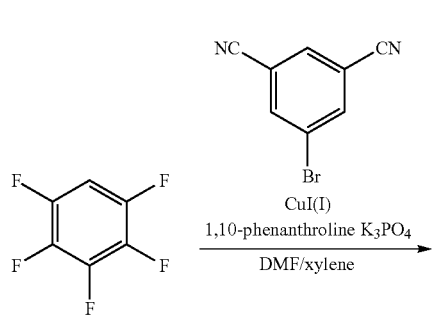

-continued

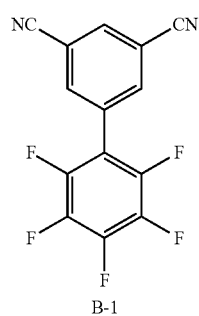

Intermediate B-1 was synthesized by performing the same procedure as in the synthetic method of Intermediate A-1 except for using 5-bromoisophthalonitrile instead of 4-bromobenzonitrile. 11 g (yield 80%) of a white solid was obtained. The molecular weight of the separated product thus obtained was found to be 294 by FAB-MS measurement, and the production of Intermediate B-1 was confirmed.

Synthesis of Intermediate B-2

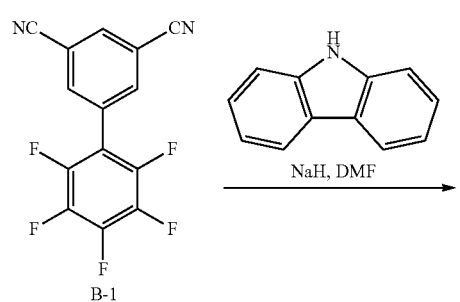

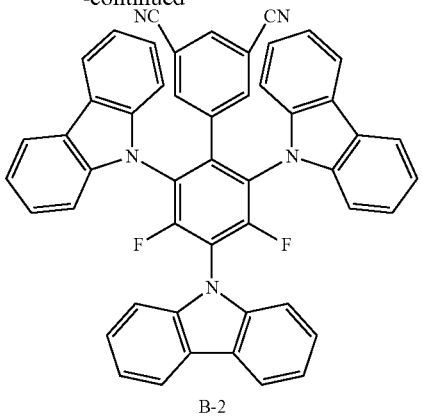

B-2

Intermediate B-2 was synthesized by performing the same procedure as in the synthetic method of Intermediate A-2 except for using Intermediate B-1 instead of Intermediate A-1, and carbazole instead of 3,6-diphenyl carbazole. 0.53 g (yield 21%) of a pale yellow solid was obtained. The molecular weight of the separated product thus obtained was found to be 736 by FAB-MS measurement, and the production of Intermediate B-2 which was a target material was confirmed.

Synthesis of Compound 3

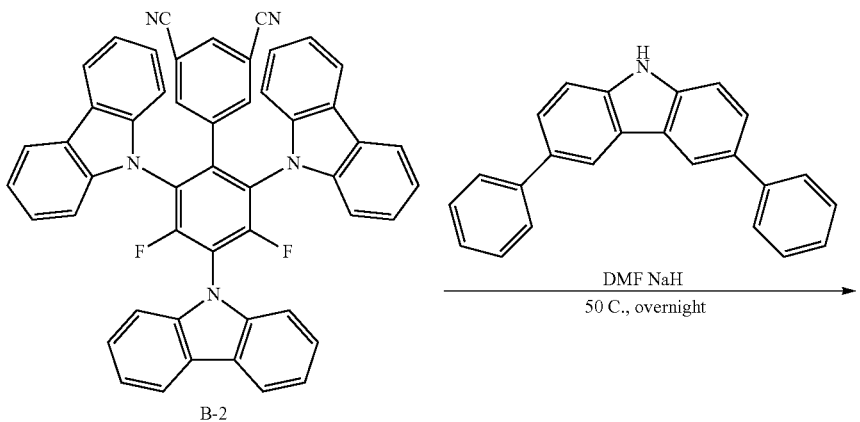

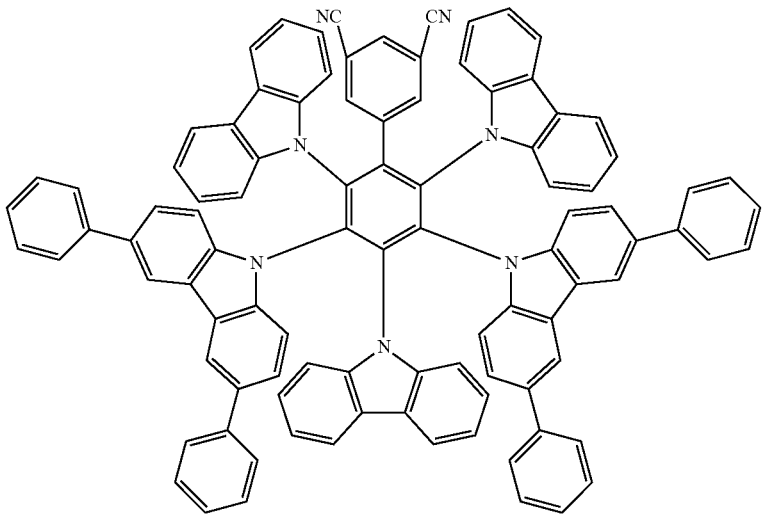

3

Compound 3 was synthesized by performing the same procedure as in the synthetic method of Compound 1 except for using Intermediate B-2 instead of Intermediate A-2, and 3,6-diphenyl carbazole instead of carbazole. 0.34 g (yield 63%) of a pale yellow solid was obtained. The molecular weight of the separated product thus obtained was found to be 1335 by FAB-MS measurement, and the production of Compound 3 was confirmed.

(Synthesis of Compound 4)

<Synthesis of Intermediate C-1>

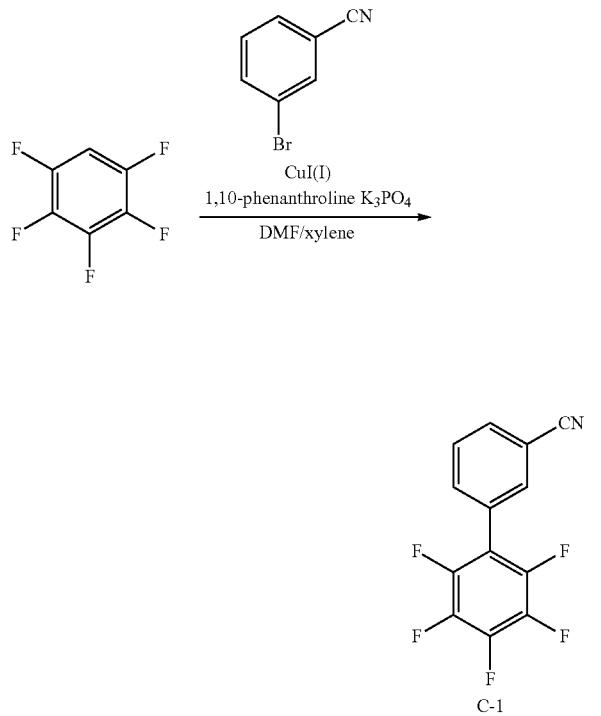

Intermediate C-1 was synthesized by performing the same procedure as in the synthetic method of Intermediate A-1 except for using 3-bromobenzonitrile instead of 4-bromobenzonitrile. 11 g (yield 76%) of a white solid was obtained. The molecular weight of the separated product thus obtained was found to be 269 by FAB-MS measurement, and the production of Intermediate C-1 which was a target material was confirmed.

<Synthesis of Intermediate C-2>

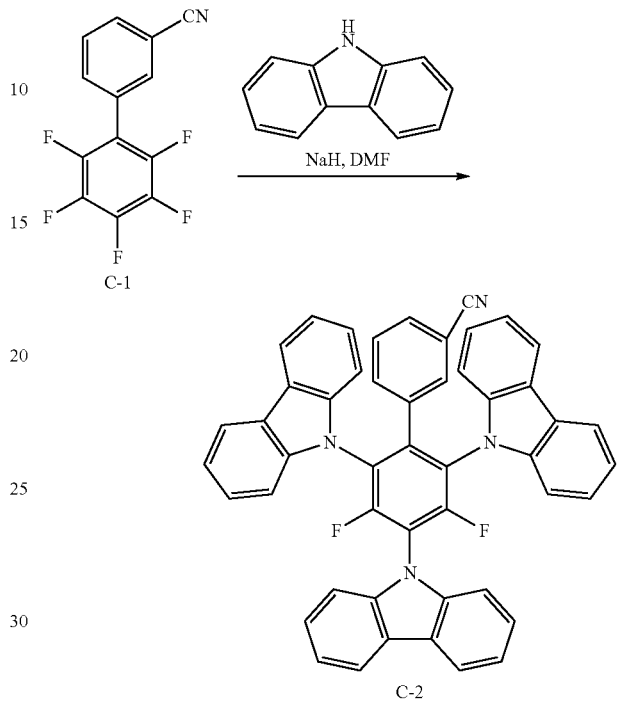

Intermediate C-2 was synthesized by performing the same procedure as in the synthetic method of Intermediate A-2 except for using Intermediate C-1 instead of Intermediate A-1, and using carbazole instead of 3,6-diphenyl carbazole. 0.37 g (yield 14%) of a pale yellow solid was obtained. The molecular weight of the separated product thus obtained was found to be 711 by FAB-MS measurement, and the production of Intermediate C-2 which was a target material was confirmed.

<Synthesis of Compound 4>

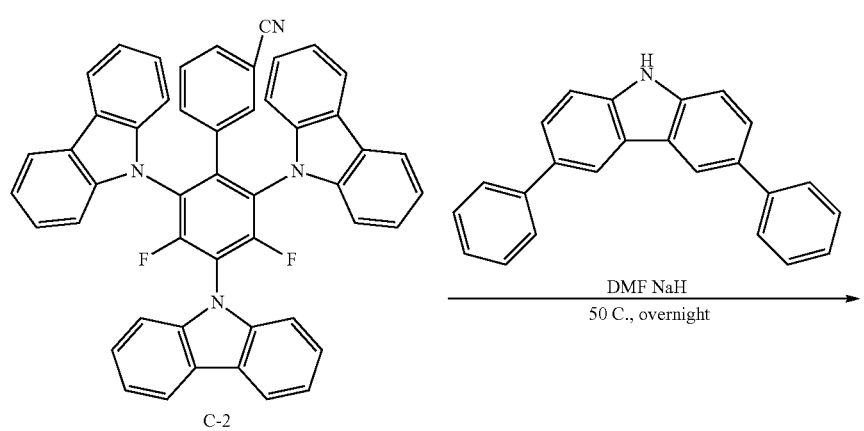

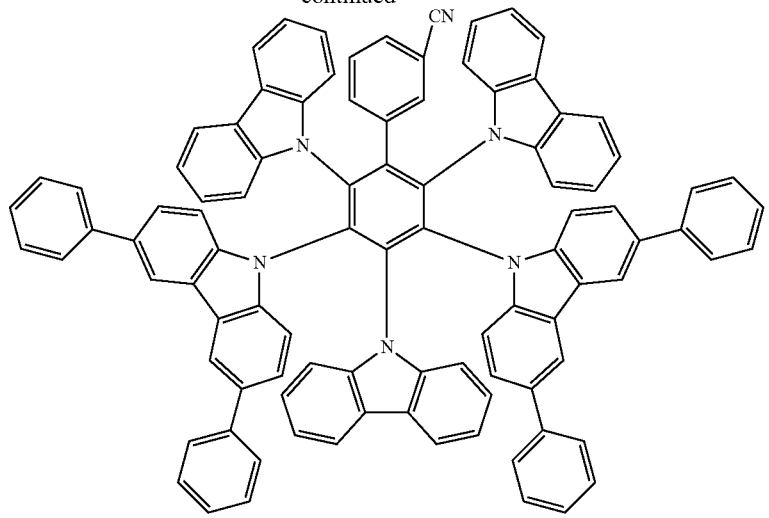

4

Compound 4 was synthesized by performing the same procedure as in the synthetic method of Compound 1 except for using Intermediate C-2 instead of Intermediate A-2, and using 3,6-diphenyl carbazole instead of carbazole. 0.41 g (yield 76%) of a pale yellow solid was obtained. The molecular weight of the separated product thus obtained was found to be 1310 by FAB-MS measurement, and the production of Compound 4 was confirmed.

2. Evaluation of Energy Level of Compounds

In Table 1 below, the lowest singlet excitation energy levels (S1 level), the lowest triplet excitation energy levels (T1 level), and $E_{ST}$ values are shown for Compound 1 to Compound 4, which are the Example Compounds, and Comparative Compound C1 below.

Comparative Compound

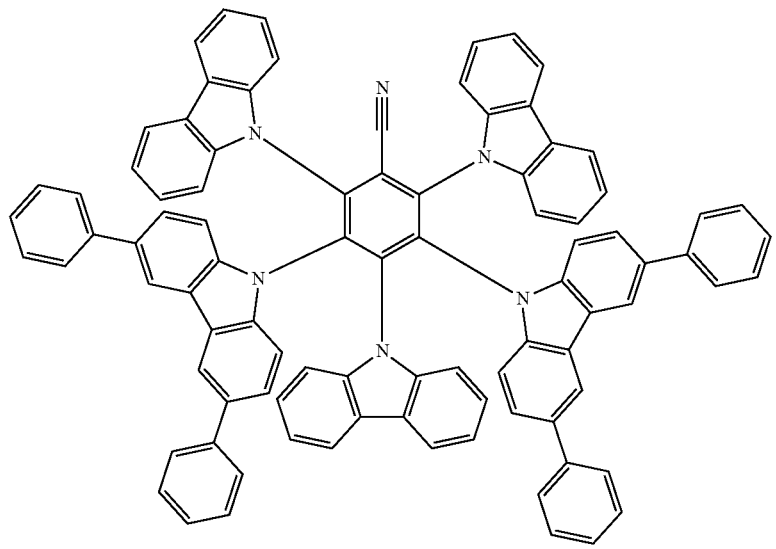

C1

In Table 1, the energy level value was calculated by non-empirical molecular orbital method. Particularly, the calculation was carried out by B3LYP/6-31G(d) using Gaussian 09 of Gaussian Co. $E_{ST}$ represents a difference between the lowest singlet excitation energy level (S1 level) and the lowest triplet excitation energy level (T1 level).

TABLE 1

| Compound | S1 level (eV) | T1 level (eV) | $E_{ST}$ (eV) |
|---|---|---|---|
| Compound 1 | 2.87 | 2.73 | 0.14 |
| Compound 2 | 2.92 | 2.75 | 0.17 |
| Compound 3 | 3.01 | 2.79 | 0.22 |
| Compound 4 | 3.86 | 2.71 | 0.15 |
| Comparative Compound C1 | 2.60 | 2.46 | 0.14 |

Compound 1 to Compound 4, which are Example Compounds, have an $E_{ST}$ value of about 0.25 eV or less. From the results, it is considered that Compound 1 to Compound 4 may be used as thermally activated delayed fluorescence dopant materials. In addition, Comparative Compound C1 also showed a low $E_{ST}$ value and is considered to be used as a thermally activated delayed fluorescence dopant material.

3. Evaluation of Fluorescence Emission Properties of the Compounds

Fluorescence emission properties were evaluated using a V-670 spectrometer of JASCO Co. An organic layer was formed on a quartz glass by co-depositing PPF represented below as a host material, and each of Compound 1 to Compound 4 and Comparative Compound C1 as a dopant material.

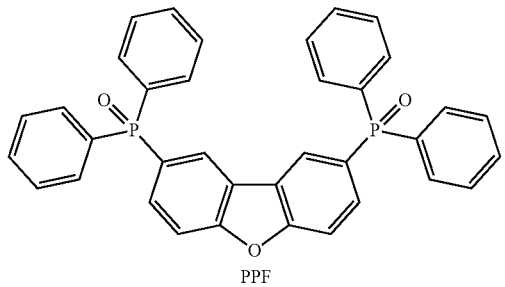

PPF

The ratio of the co-deposited host and dopant was 80:20. With respect to the organic layer thus manufactured, fluorescence emission spectrum was measured. The fluorescence quantum yield was measured using ILF-835 integrating sphere system of JASCO Co.

Table 2 below shows fluorescence emission properties for the Examples and the Comparative Example, and in the evaluation of the fluorescence emission properties, $\lambda_{max}$ represents emission central wavelength which represents the maximum emission intensity in light-emitting peaks.

TABLE 2

| Division | Dopant material | $\lambda_{max}$ (nm) | Fluorescence quantum yield (%) |
|---|---|---|---|
| Example 1 | Compound 1 | 450 | 85 |
| Example 2 | Compound 2 | 443 | 78 |
| Example 3 | Compound 3 | 430 | 80 |
| Example 4 | Compound 4 | 452 | 75 |

TABLE 2-continued

| Division | Dopant material | $\lambda_{max}$ (nm) | Fluorescence quantum yield (%) |
|---|---|---|---|
| Comparative Example 1 | Comparative Compound C1 | 495 | 80 |

Referring to the results of Table 2, Example 1 to Example 4 showed similar degrees of fluorescence quantum yield as that of Comparative Example 1. The emission central wavelength of Example 1 to Example 4 ($\lambda_{max}$) was found to correspond to a short wavelength region when compared with the emission central wavelength of Comparative Example 1. Thus, from the results of Table 2, the Example Compounds were found to emit deep blue light which is blue light in a short wavelength region when compared with Comparative Compound C1.

4. Manufacture and Evaluation of Organic Electroluminescence Device (Manufacture of Organic Electroluminescence Devices)

Organic electroluminescence devices of example embodiments including the compounds of example embodiments in an emission layer were manufactured by a method described below. Organic electroluminescence devices of Examples 1 to 4 were manufactured using the compounds of Compound 1 to Compound 4 as dopant materials for an emission layer. The organic electroluminescence device of the Comparative Example was manufactured using Comparative Compound C1 as a dopant material in an emission layer.

On a glass substrate, ITO with a thickness of about 1,500 Å was patterned and washed with ultra-pure water, washed with ultrasonic waves, exposed to UV for about 30 minutes and treated with ozone. Then, 1,4,5,8,9,11-hexaazatriphenylenehexacarbonitrile (HAT-CN) was deposited to a thickness of about 100 Å to form a hole injection layer, and N,N'-di(1-naphthyl)-N,N'-diphenyl-(1,1'-biphenyl)-4,4'-diamine (NPB) was deposited to a thickness of about 800 Å to form a hole transport layer. Then, 1,3-bis(N-carbazolyl)benzene (mCBP) was deposited to a thickness of about 50 Å to form an electron blocking layer.

On the electron blocking layer, bis[2-(diphenylphosphino)phenyl] ether oxide (DPEPO) and each of the Example Compounds or the Comparative Compound were co-deposited in a ratio of 80:20 to form an emission layer to a thickness of about 200 Å. Thus, the emission layer was formed by the co-deposition of Compounds 1, 2, 3 or 4 with DPEPO in Example 1 to Example 4, or Comparative Compound C1 with DPEPO in Comparative Example 1.

On the emission layer, a hole blocking layer was formed using DPEPO to a thickness of about 100 Å, and then, an electron transport layer was formed using 2,2',2"-(1,3,5-benzinetriyl)-tris(1-phenyl-1-H-benzimidazole (TPBi) to a thickness of about 300 Å. Then, an electron injection layer was formed using 8-hydroxyquinolinolato-lithium (Liq) to a thickness of about 10 Å. Then, a second electrode was formed using aluminum (Al) to a thickness of about 1,000 Å.

In the Examples, the hole injection layer, the hole transport region, the electron blocking layer, the emission layer, the hole blocking layer, the electron transport layer, the electron injection layer and the second electrode were formed by using a vacuum deposition apparatus.

(Evaluation of Properties of Organic Electroluminescence Device)

In Table 3, the evaluation results on the organic electroluminescence devices of Example 1 to Example 4 and Comparative Example 1 are shown. In Table 3 $\lambda_{max}$ which is the emission central wavelength, emission efficiency and life of the organic electroluminescence device thus manufactured are compared and shown. In the evaluation results of the properties on the Examples and the Comparative Example, as shown in Table 3, voltage and current density were measured using a source meter (2400 series, Keithley Instrument Co.), luminance and external quantum efficiency were measured using an external quantum efficiency measurement apparatus, C9920-12 of HAMAMATSU Photonics Co. The emission efficiency represents a current efficiency value with respect to current density of 10 mA/cm$^2$, and the life represents half life at 1.0 mA/cm$^2$.

The emission efficiency and life are compared and shown as relative values in Table 3. The emission efficiency and life in the Examples are relative to the emission efficiency and life in Comparative Example 1 (which are set to 1).

TABLE 3

| Division | Dopant material | $\lambda_{max}$ (nm) | Emission efficiency | Life |
| --- | --- | --- | --- | --- |
| Example 1 | Compound 1 | 453 | 1.03 | 0.95 |
| Example 2 | Compound 2 | 442 | 0.98 | 1.01 |
| Example 3 | Compound 3 | 435 | 0.95 | 0.91 |
| Example 4 | Compound 4 | 454 | 0.96 | 0.95 |
| Comparative Example 1 | Comparative Compound C1 | 497 | 1 | 1 |

Referring to the results in Table 3, the organic electroluminescence devices of Example 1 to Example 4 were found to show similar degree of emission efficiency and life characteristics as those of the organic electroluminescence device of Comparative Example 1. However, from the point that the organic electroluminescence devices of Example 1 to Example 4 showed emission maximum peak, $\lambda_{max}$, in a short wavelength region when compared with the organic electroluminescence device of Comparative Example 1, it was found that Example 1 to Example 4 emitted deep blue light which was blue light with a short wavelength when compared with Comparative Example 1.

Referring to the evaluation results of the Example Compounds and the Examples of the organic electroluminescence devices, it was found that the compounds according to example embodiments may be used as a material emitting deep blue light and may show excellent life characteristics. In addition, in the organic electroluminescence device according to example embodiments (which included the compound according to example embodiments in an emission layer), excellent emission efficiency properties and life characteristics were shown while emitting deep blue light.

By way of summation and review, in the application of an organic electroluminescence device to a display device, a decrease of the driving voltage, and an increase of the emission efficiency and the life of the organic electroluminescence device are desired.

In an effort to provide an organic electroluminescence device with high efficiency, techniques on phosphorescence emission (which uses energy in a triplet state) or delayed fluorescence emission (which uses the generating phenomenon of singlet excitons by the collision of triplet excitons (triplet-triplet annihilation, TTA)) are being considered, and suitable materials for thermally activated delayed fluorescence (TADF) using delayed fluorescence phenomenon are of interest.

As described above, embodiments relate a compound used as a light-emitting material and an organic electroluminescence device including the same.

Without being bound by theory, it is believed that, in a compound according to an example embodiment that includes a phenyl group as a linker between a cyano group which is an electron acceptor and a phenyl group in which a carbazole group is substituted as an electron donor, the electron accepting properties of the cyano group may be weakened, and thus, may be used as a light-emitting material showing excellent life characteristics and emitting deep blue light. In addition, in an organic electroluminescence device according to an example embodiment (including a compound according to an example embodiment in an emission layer) may show excellent emission efficiency and life characteristics while emitting deep blue light.

An organic electroluminescence device according to an example embodiment may emit deep blue light and show excellent life characteristics.

A compound according to an example embodiment may be included in an emission layer of an organic electroluminescence device and may emit deep blue light.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic electroluminescence device, comprising:
   a first electrode;
   a second electrode on the first electrode; and
   an emission layer between the first electrode and the second electrode,
   wherein the emission layer includes a compound including a first phenyl group that is substituted with at least one cyano group and a second phenyl group that is substituted with five substituted or unsubstituted carbazole groups, the second phenyl group being directly bonded to the first phenyl group.

2. The organic electroluminescence device as claimed in claim 1, wherein the at least one cyano group is substituted on the first phenyl group at a para position or a meta position with respect to the second phenyl group.

3. The organic electroluminescence device as claimed in claim 1, wherein the five substituted or unsubstituted carbazole groups are selected from an unsubstituted carbazole group, a carbazole group that is substituted with an aryl group of 6 to 18 ring carbon atoms, or a carbazole group that is substituted with a heteroaryl group of 5 to 18 ring carbon atoms.

4. The organic electroluminescence device as claimed in claim 1, wherein the second phenyl group is substituted with at least one of a carbazole group that is substituted with a phenyl group, or a carbazole group that is substituted with a pyridine group.

5. The organic electroluminescence device as claimed in claim 1, wherein the compound is represented by the following Formula 1:

[Formula 1]

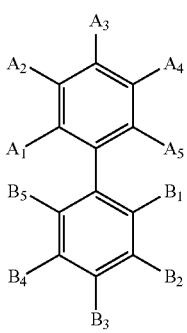

wherein, in Formula 1,
at least one among $A_1$ to $A_5$ is a cyano group, and the rest are each independently a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms,
at least one among $B_1$ to $B_5$ is represented by the following Formula 2-1 and the rest are represented by the following Formula 2-2:

[Formula 2-1]

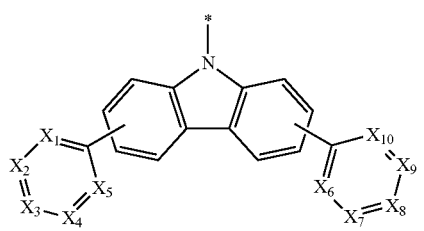

[Formula 2-2]

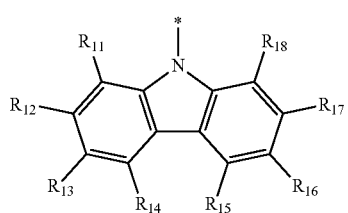

wherein, in Formula 2-1, $X_1$ to $X_{10}$ are each independently N or $CR_1$, and
$R_1$ is a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms,
wherein, in Formula 2-2,
$R_{11}$ to $R_{18}$ are each independently a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms.

6. The organic electroluminescence device as claimed in claim 5, wherein Formula 1 is represented by any one among the following Formula 1-1 to Formula 1-3:

[Formula 1-1]

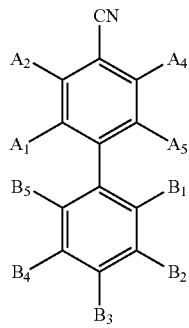

[Formula 1-2]

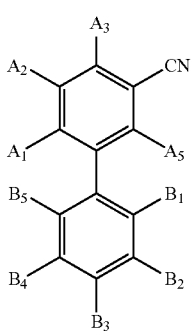

[Formula 1-3]

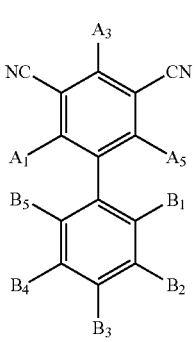

wherein, in Formula 1-1 to Formula 1-3, $A_1$ to $A_5$, and $B_1$ to $B_5$ are the same as defined in Formula 1.

7. The organic electroluminescence device as claimed in claim 5, wherein Formula 1 is represented by the following Formula 1-4 or Formula 1-5:

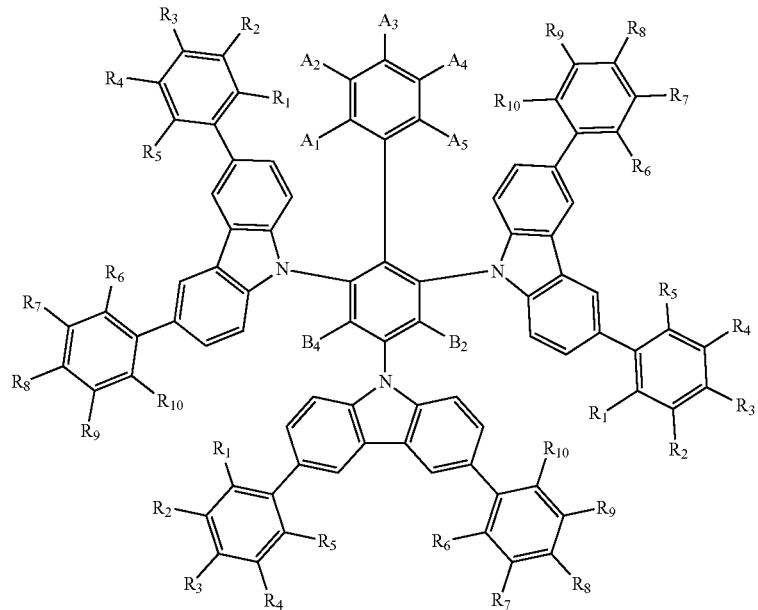
[Formula 1-4]
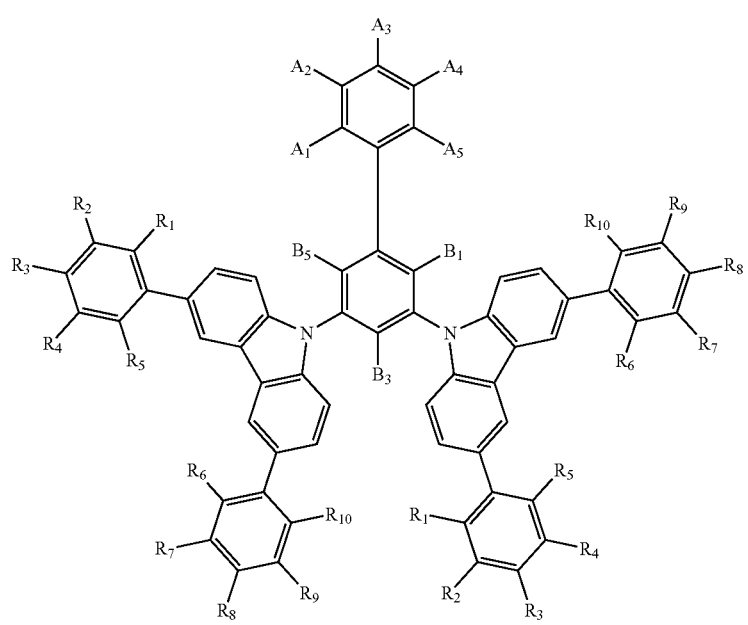
[Formula 1-5]

wherein, in Formula 1-4, $B_2$ and $B_4$ are represented by Formula 2-2, in Formula 1-5, $B_1$, $B_3$, and $B_5$ are represented by Formula 2-2, and in Formula 1-4 and Formula 1-5, $A_1$ to $A_5$ are the same as defined in Formula 1.

8. The organic electroluminescence device as claimed in claim 5, wherein Formula 2-1 is represented by the following Formula 2-1A or Formula 2-1B, and Formula 2-2 is represented by the following Formula 2-2A:

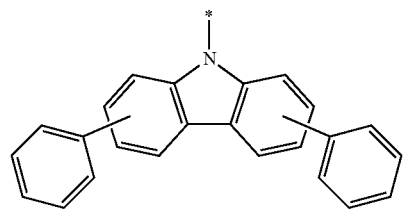

[Formula 2-1A]

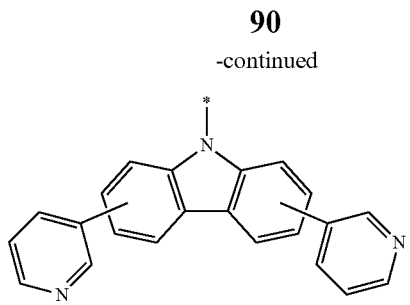

[Formula 2-1B]

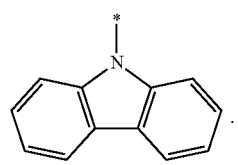

[Formula 2-2A]

9. The organic electroluminescence device as claimed in claim 1, wherein the emission layer emits light by delayed fluorescence.

10. The organic electroluminescence device as claimed in claim 1, wherein the emission layer is a delayed fluorescence emission layer including a host and a dopant, and the dopant includes the compound.

11. The organic electroluminescence device as claimed in claim 1, wherein the emission layer emits blue light having a central wavelength $\lambda_{max}$ of 430 nm to 490 nm.

12. The organic electroluminescence device as claimed in claim 1, wherein the emission layer includes at least one among compounds in the following Compound Group 1:

[Compound Group 1]

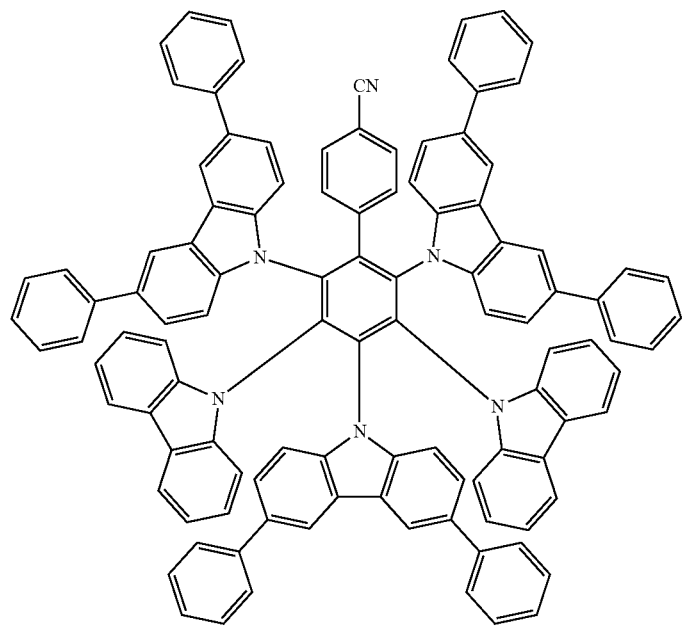

1

-continued
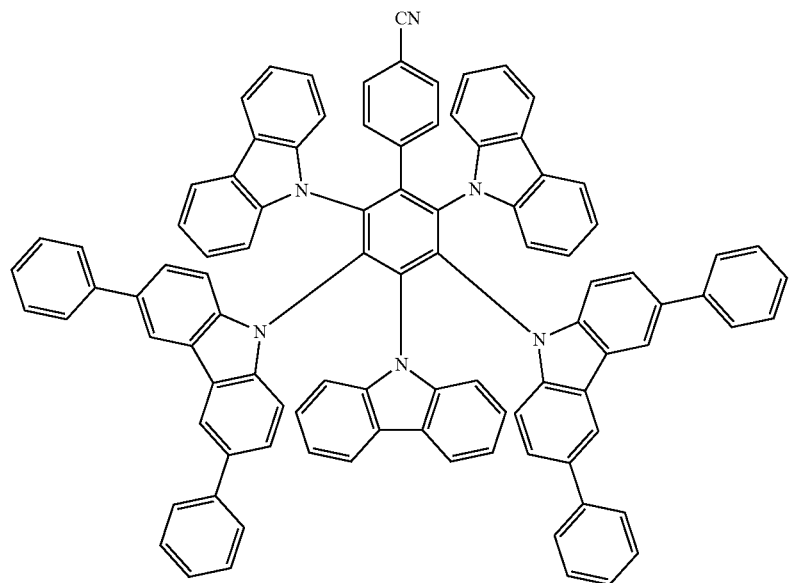
2
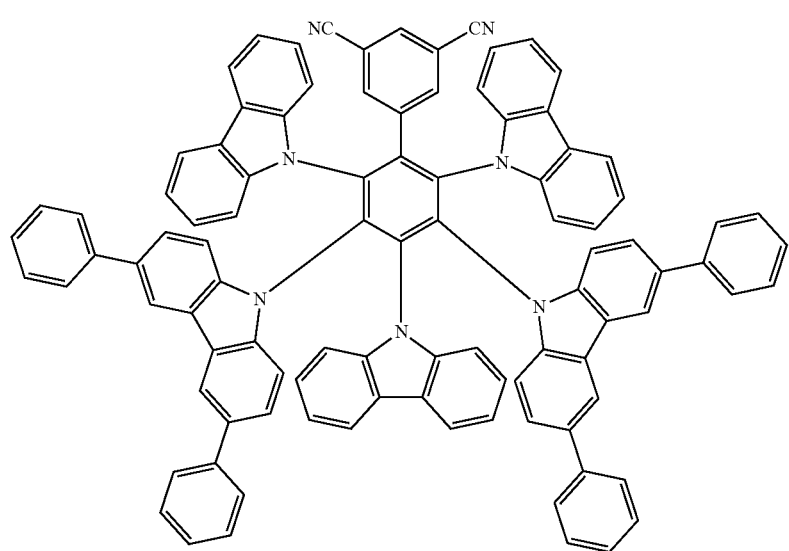
3
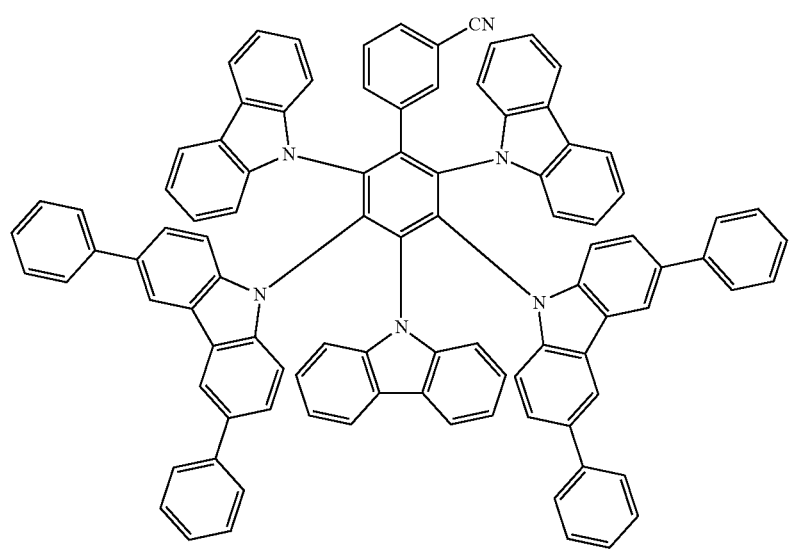
4

-continued
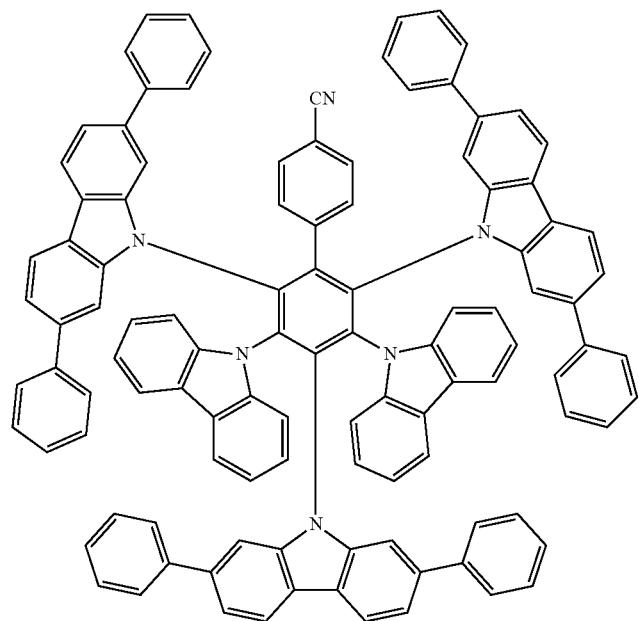
5
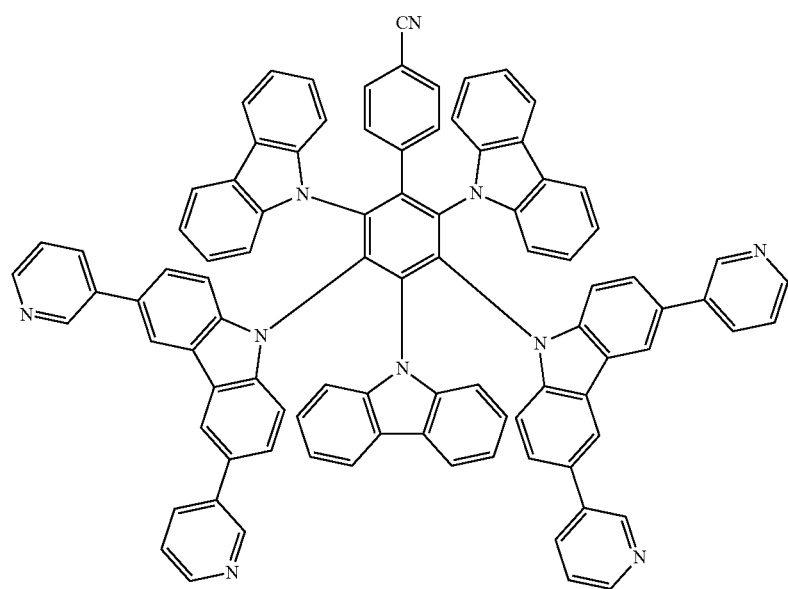
6

-continued
7
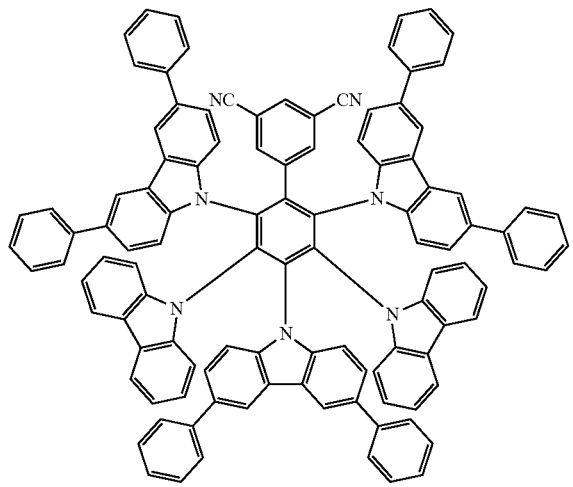
8
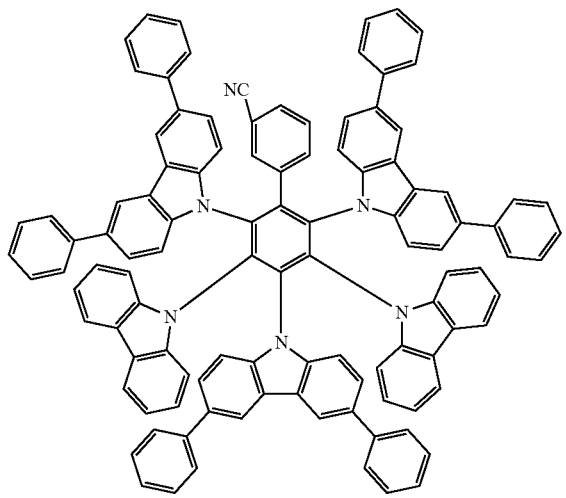
9
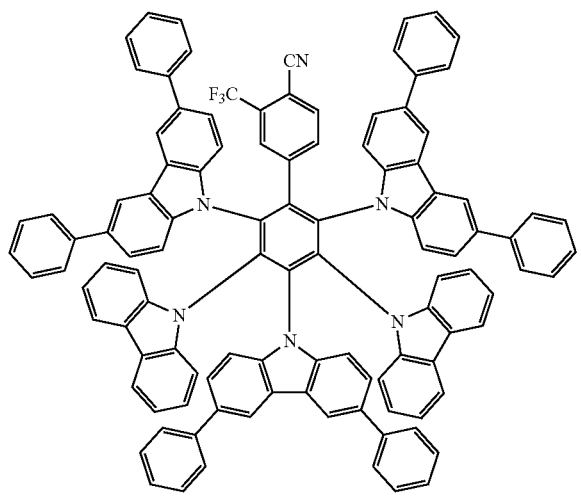
10
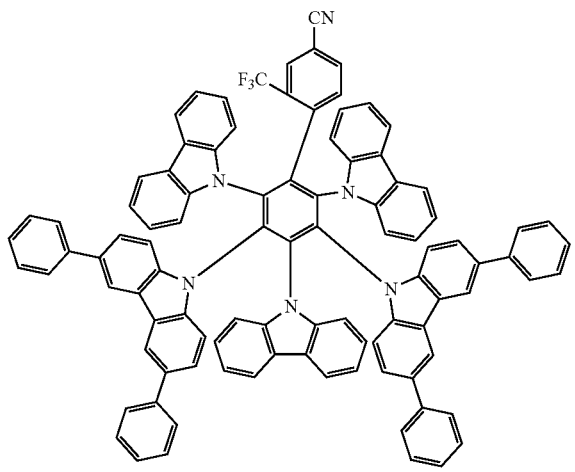
11
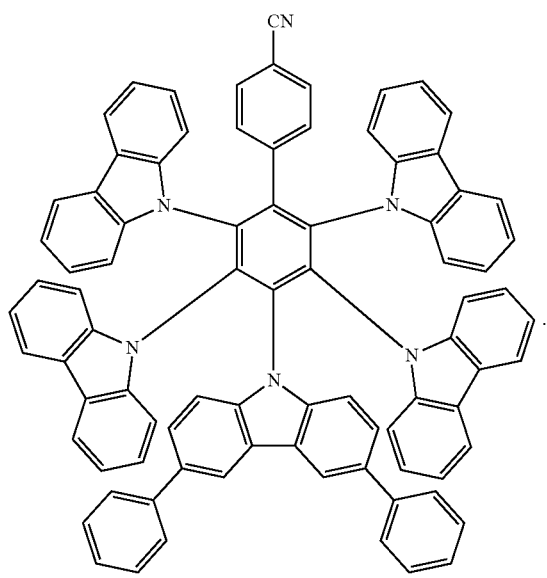

13. An organic electroluminescence device, comprising:
a first electrode;
a second electrode on the first electrode; and
an emission layer between the first electrode and the second electrode, the emission layer including a compound represented by the following Formula 1:

[Formula 1]

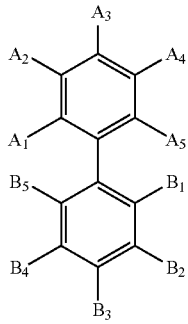

wherein, in Formula 1,
at least one among $A_1$ to $A_5$ is a cyano group, and the rest are each independently a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms,
at least one among $B_1$ to $B_5$ is represented by the following Formula 2-1 and the rest are represented by the following Formula 2-2:

[Formula 2-1]

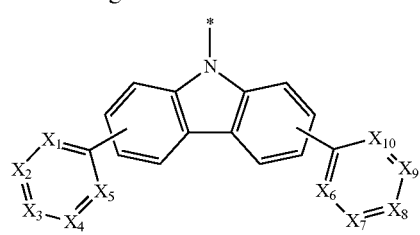

[Formula 2-2]

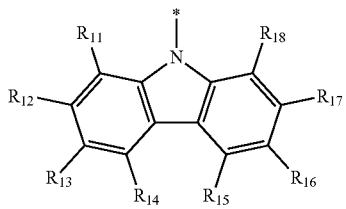

wherein, in Formula 2-1, $X_1$ to $X_{10}$ are each independently N or $CR_1$, and $R_1$ is a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms, wherein, in Formula 2-2, $R_{11}$ to $R_{18}$ are each independently a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms.

14. The organic electroluminescence device as claimed in claim 13, wherein the emission layer emits blue light having a central wavelength $\lambda_{max}$ of 430 nm to 490 nm.

15. The organic electroluminescence device as claimed in claim 13, wherein the compound is at least one among compounds represented in the following Compound Group 1:

[Compound Group 1]

1

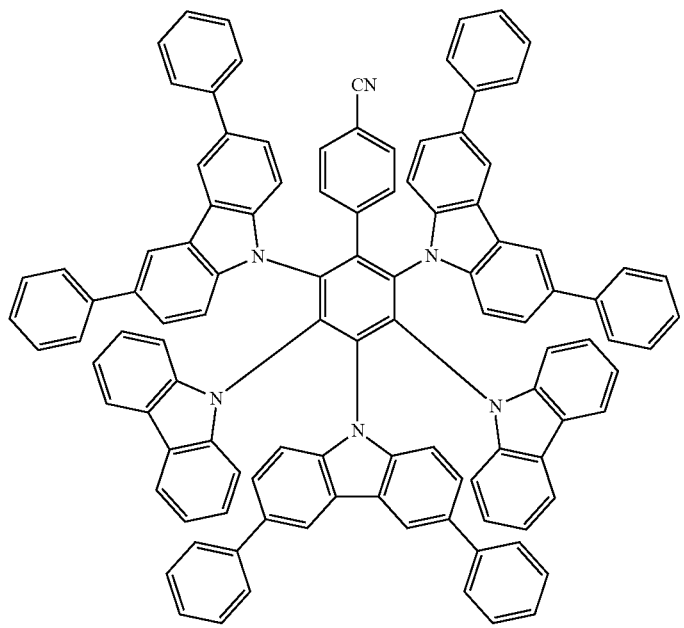

-continued
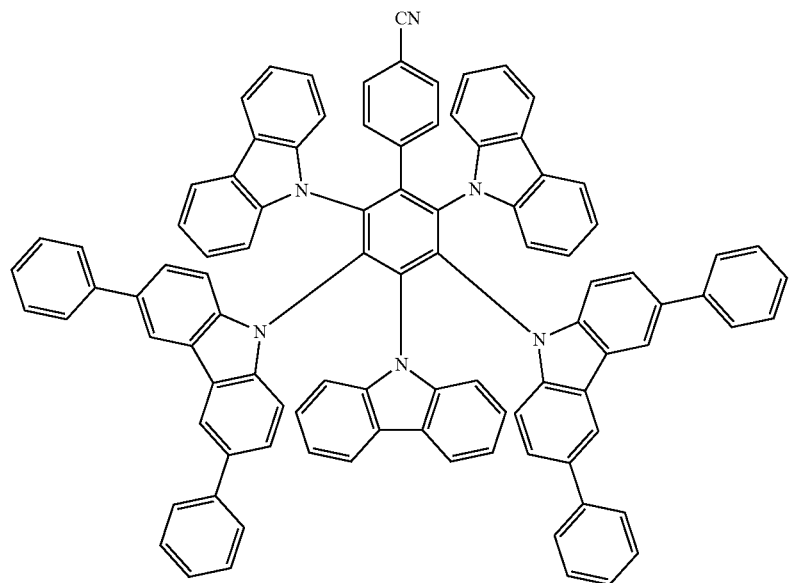
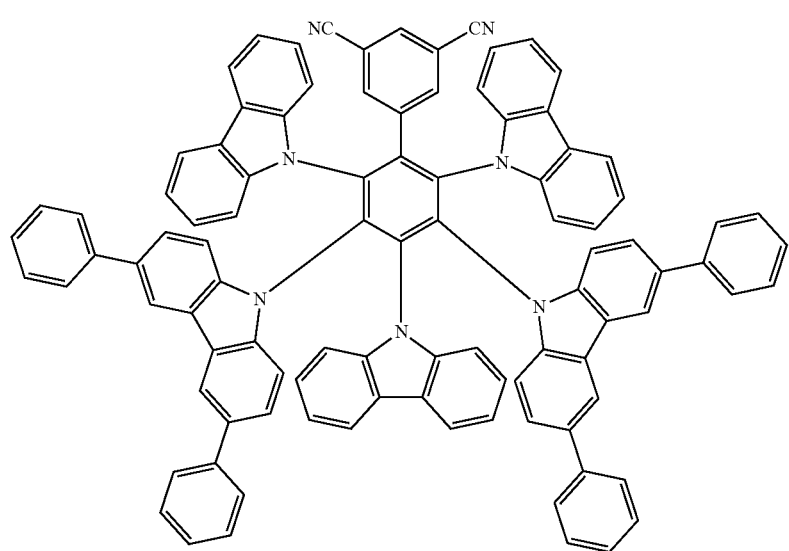
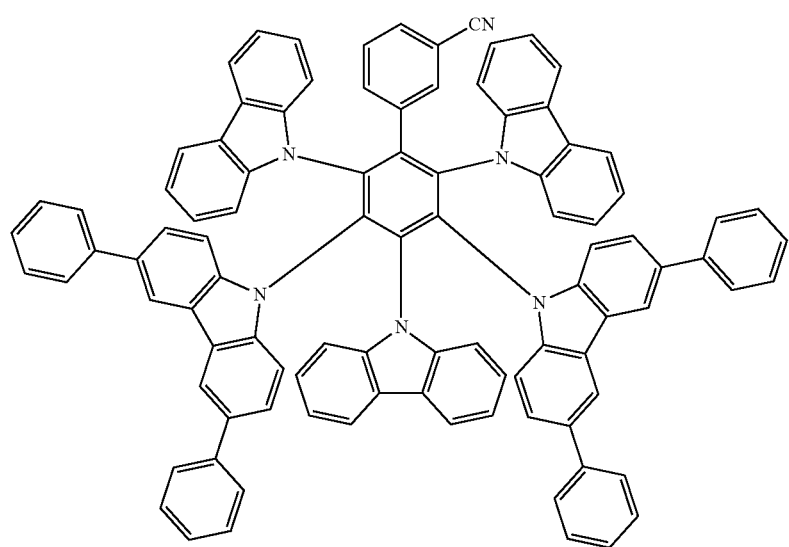

-continued
5
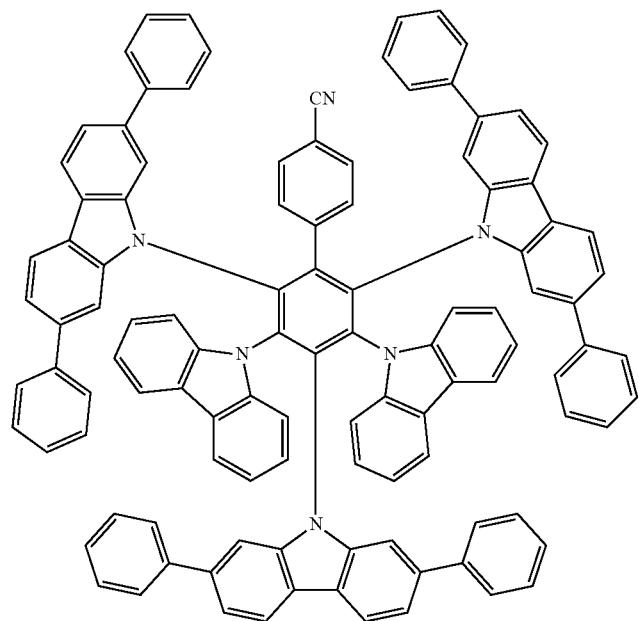
6
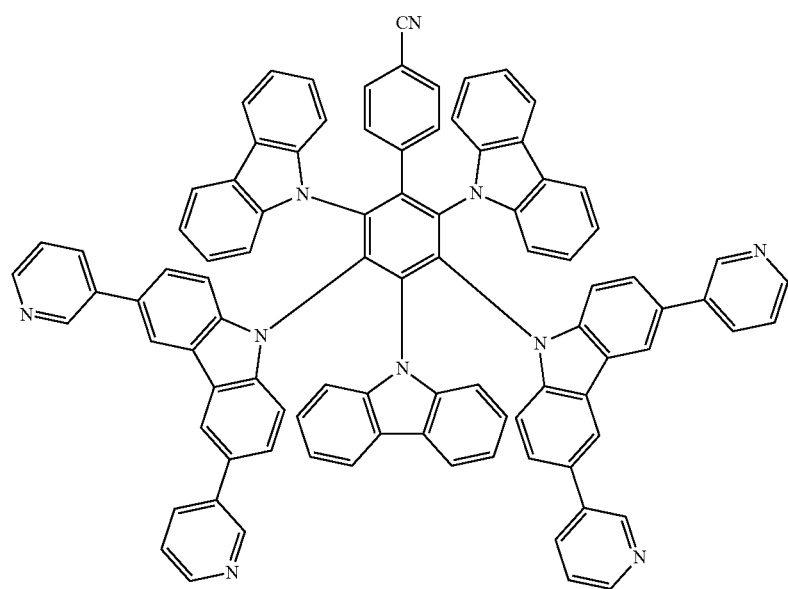

-continued
7
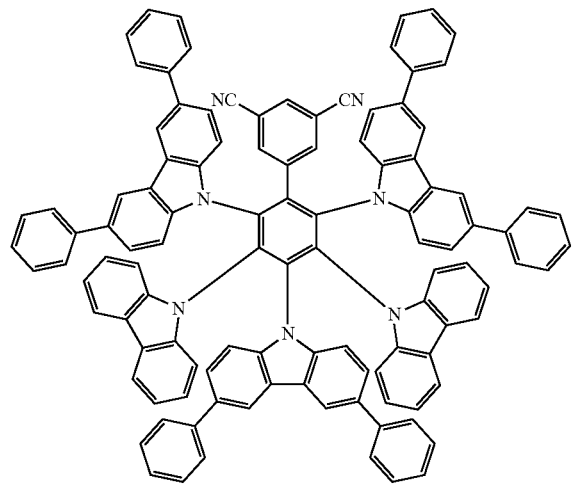
8
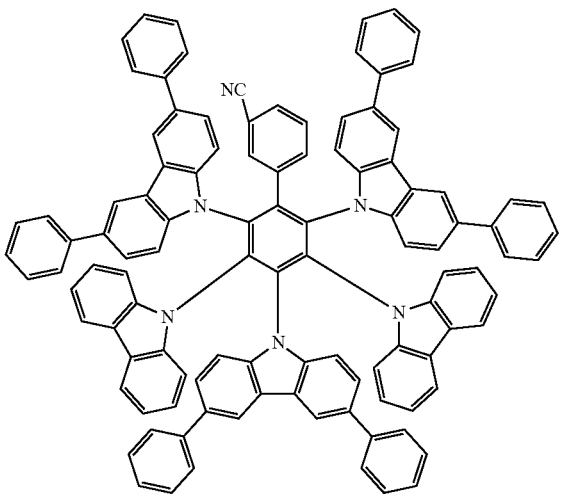
9
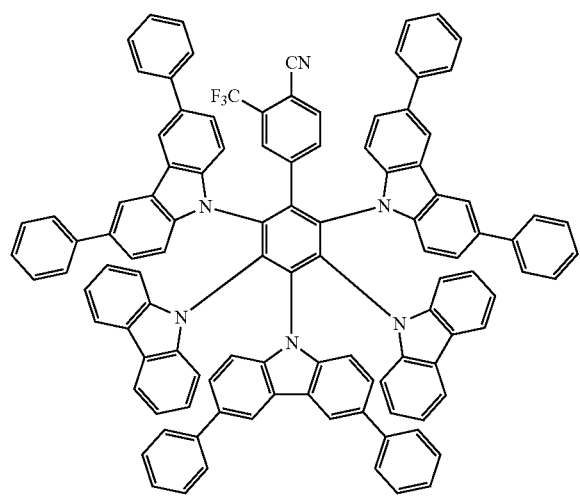
10
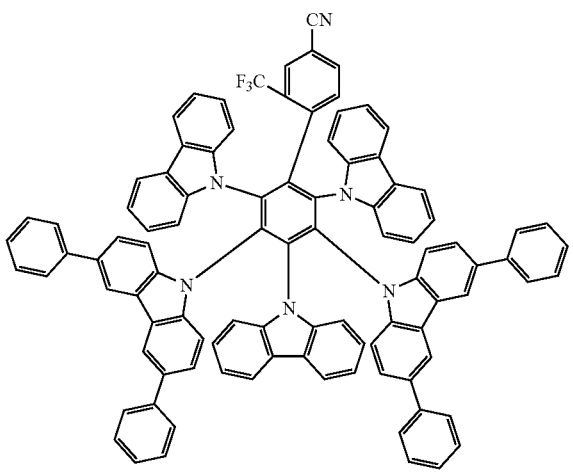
11
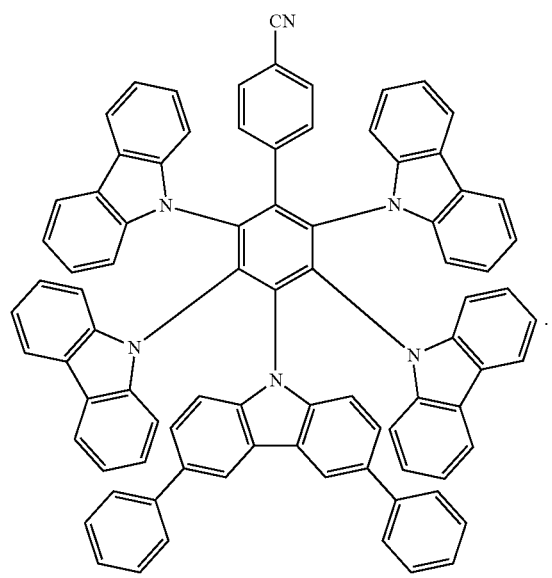

16. A compound represented by the following Formula 1:

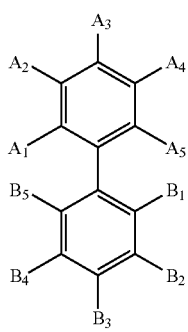

[Formula 1]

wherein, in Formula 1,
at least one among $A_1$ to $A_5$ is a cyano group, and the rest are each independently a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms,
at least one among $B_1$ to $B_5$ is represented by the following Formula 2-1 and the rest are represented by the following Formula 2-2:

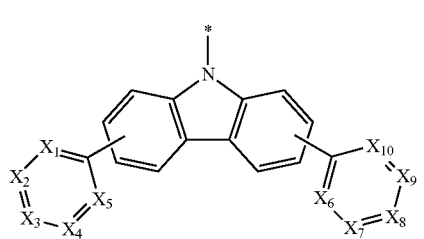

[Formula 2-1]

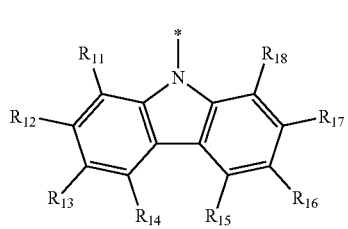

[Formula 2-2]

wherein, in Formula 2-1, $X_1$ to $X_{10}$ are each independently N or $CR_1$, and
$R_1$ is a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms,
wherein, in Formula 2-2,
$R_{11}$ to $R_{18}$ are each independently a hydrogen atom, a deuterium atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms.

17. The compound as claimed in claim 16, wherein Formula 1 is represented by any one among the following Formula 1-1 to Formula 1-3:

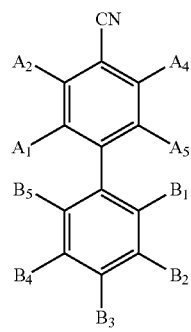

[Formula 1-1]

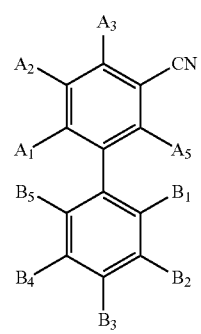

[Formula 1-2]

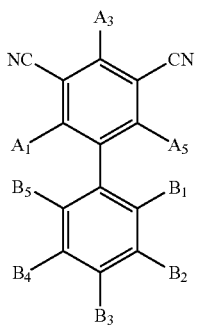

[Formula 1-3]

wherein, in Formula 1-1 to Formula 1-3, $A_1$ to $A_5$, and $B_1$ to $B_5$ are the same as defined in Formula 1.

18. The compound as claimed in claim 16, wherein Formula 1 is represented by the following Formula 1-4 or Formula 1-5:

[Formula 1-4]
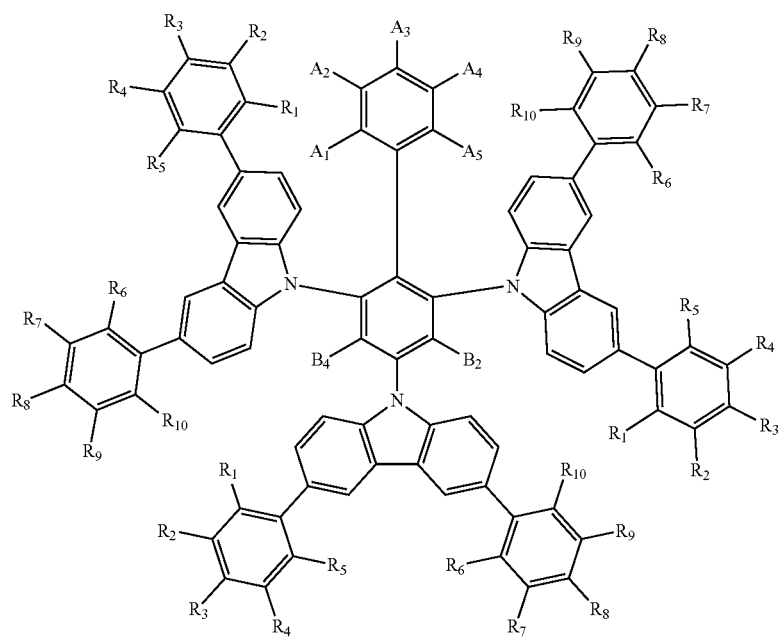
[Formula 1-5]
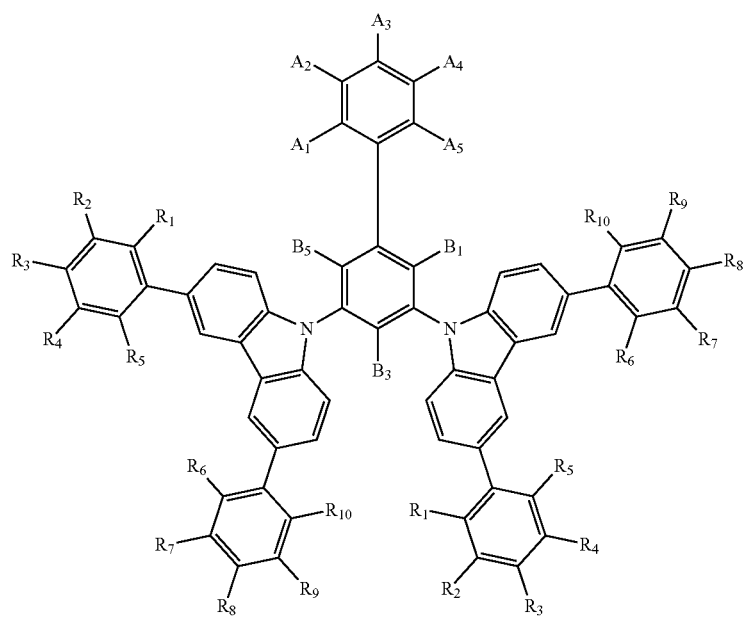

wherein,
in Formula 1-4, $B_2$ and $B_4$ are represented by Formula 2-2,
in Formula 1-5, $B_1$, $B_3$, and $B_5$ are represented by Formula 2-2, and
in Formula 1-4 and Formula 1-5, $A_1$ to $A_5$ are the same as defined in Formula 1.

19. The compound as claimed in claim 16, wherein Formula 2-1 is represented by the following Formula 2-1A or Formula 2-1B, and Formula 2-2 is represented by the following Formula 2-2A:

[Formula 2-1A]

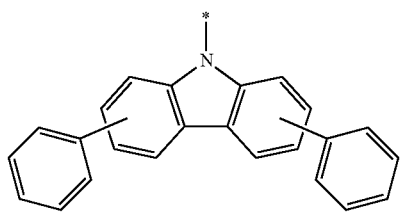

[Formula 2-1B]

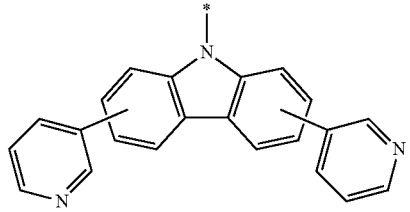

[Formula 2-2A]

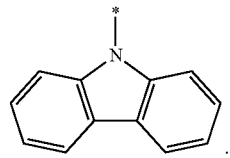

20. The compound as claimed in claim 16, wherein Formula 1 is any one among compounds in the following Compound Group 1:

[Compound Group 1]

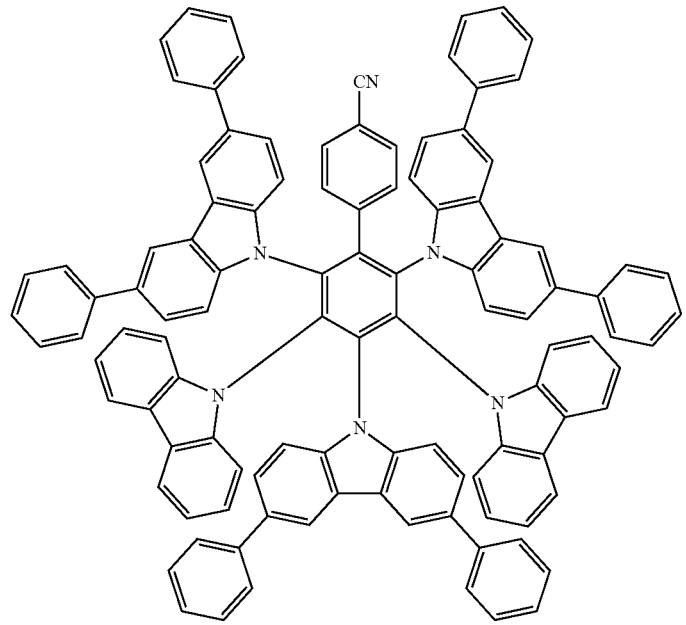

1

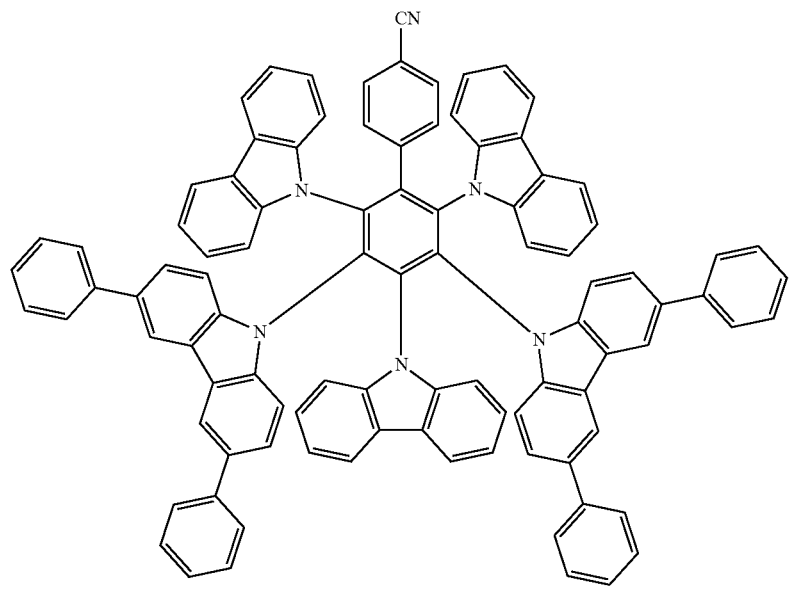
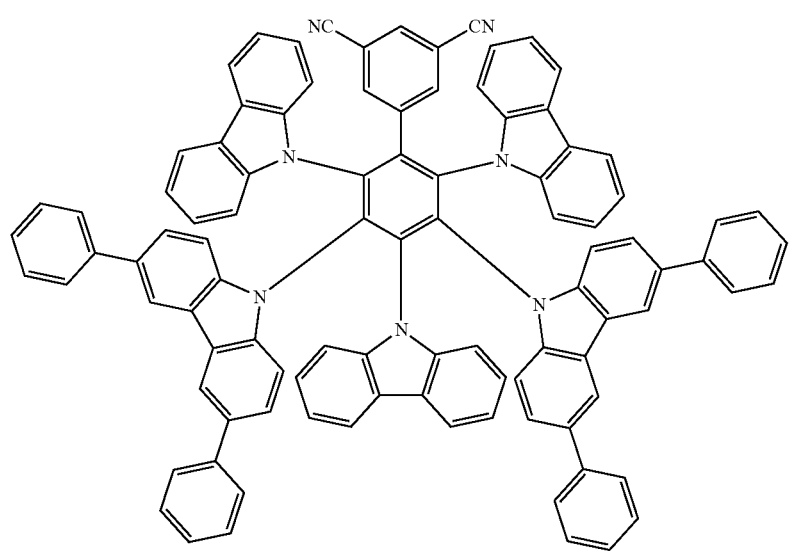
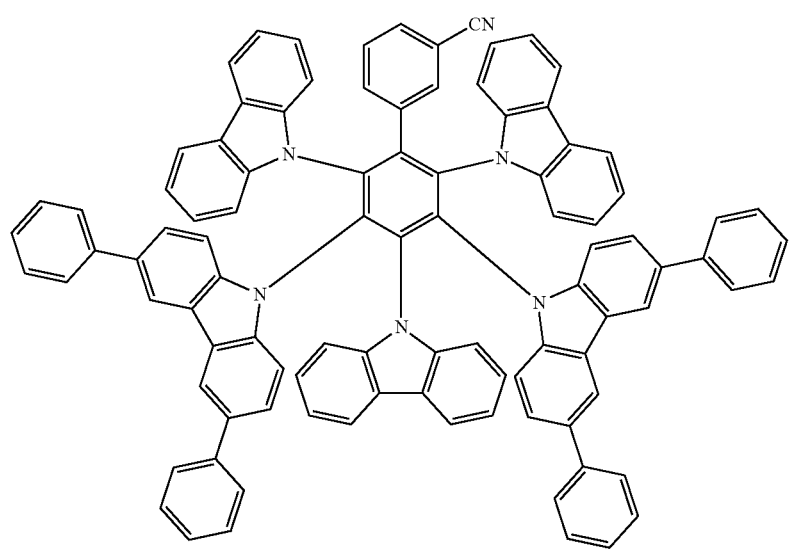

-continued
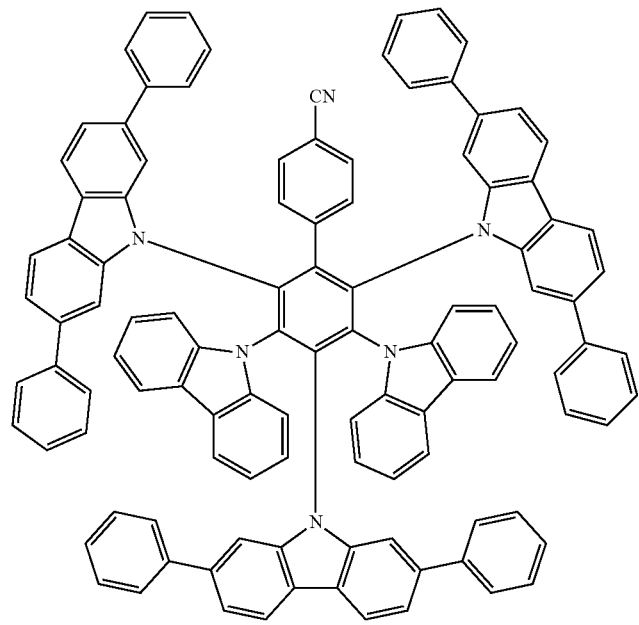
5
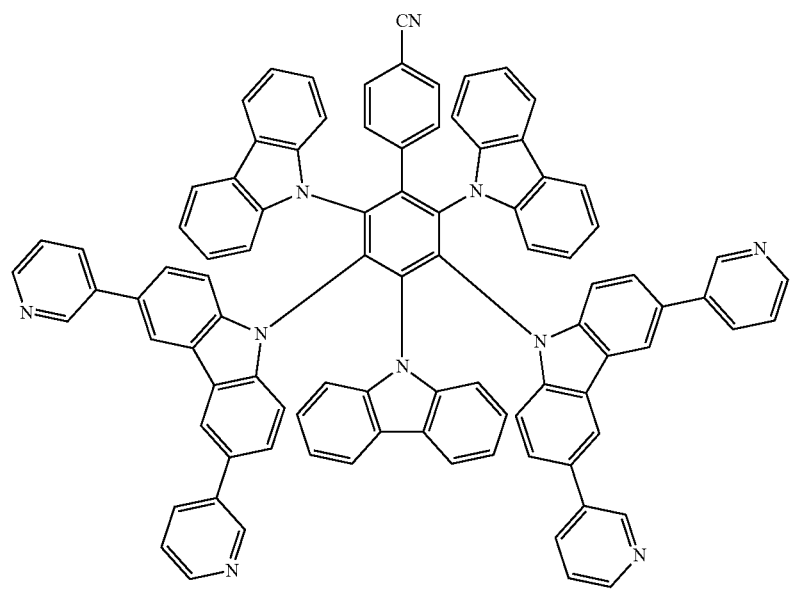
6

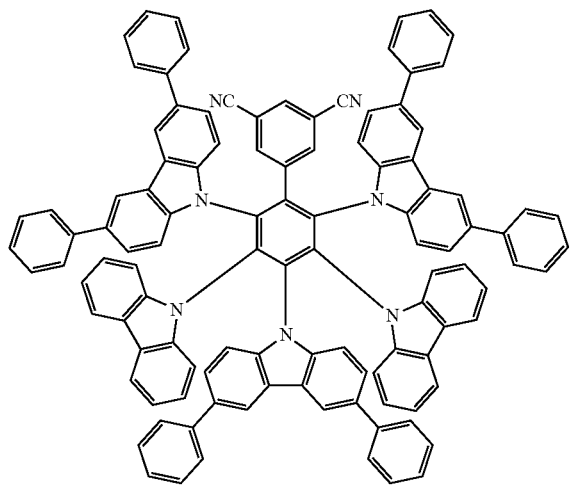
7
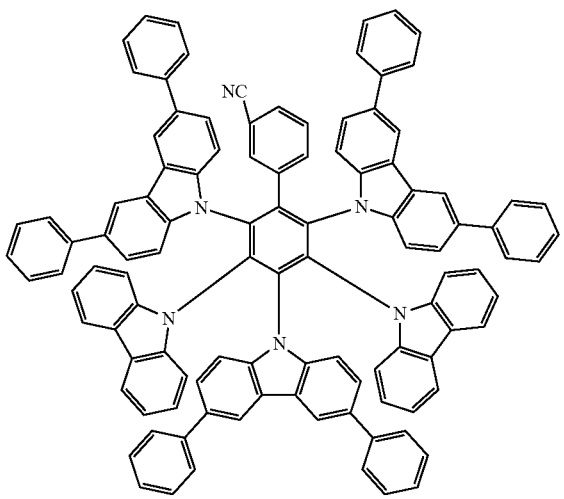
8
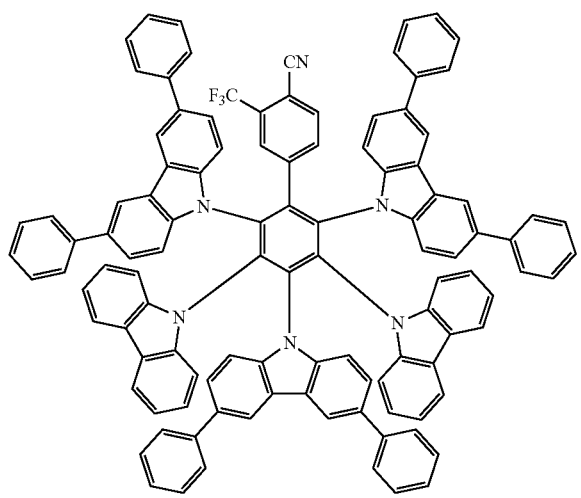
9
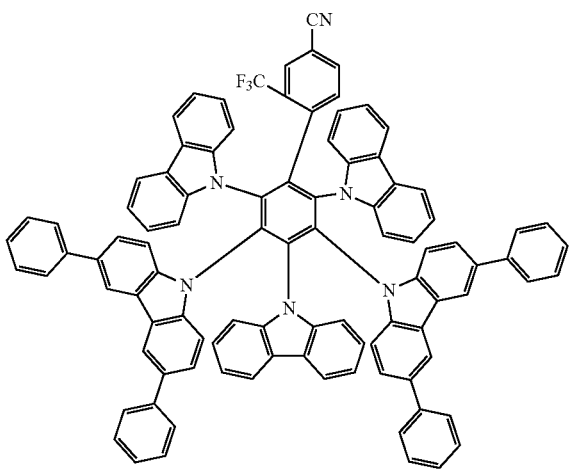
10
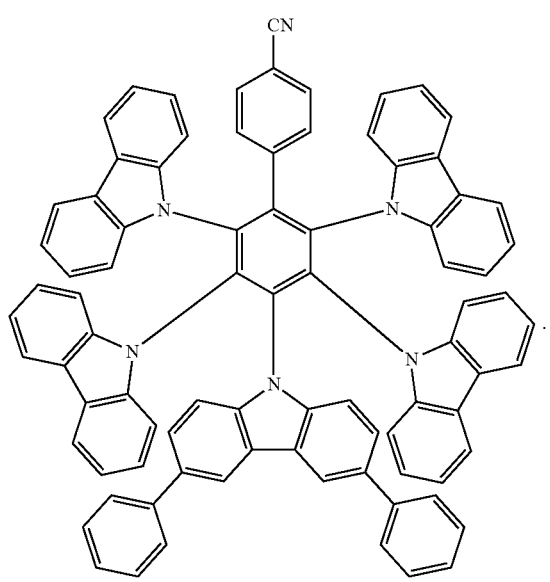
11
* * * * *